United States Patent
Paltieli et al.

(10) Patent No.: US 7,850,625 B2
(45) Date of Patent: *Dec. 14, 2010

(54) METHOD AND APPARATUS FOR MONITORING LABOR PARAMETER

(75) Inventors: Yoav Paltieli, Haifa (IL); Octavian Soldea, Kiryat Bialik (IL); Ran Bar-Sella, Haifa (IL); Gal Ben-David, Adi (IL)

(73) Assignee: Trig Medical Ltd., Yokneam Ilit (IL)

( * ) Notice: Subject to any disclaimer, the term of this patent is extended or adjusted under 35 U.S.C. 154(b) by 947 days.

This patent is subject to a terminal disclaimer.

(21) Appl. No.: 10/567,344

(22) PCT Filed: Aug. 6, 2004

(86) PCT No.: PCT/IL2004/000733

§ 371 (c)(1),
(2), (4) Date: Feb. 6, 2006

(87) PCT Pub. No.: WO2005/015499

PCT Pub. Date: Feb. 17, 2005

(65) Prior Publication Data

US 2008/0167553 A1    Jul. 10, 2008

(51) Int. Cl.
*A61B 5/103* (2006.01)
(52) U.S. Cl. ............ 600/588; 600/424; 600/425; 600/426; 600/427; 600/437; 600/443; 600/449; 600/454; 600/587; 600/591; 73/625; 73/626; 367/7; 367/11; 367/130; 128/916
(58) Field of Classification Search ........ 600/437–472, 600/424–427, 429, 587, 588, 591; 73/625, 73/626; 367/7, 11, 130; 128/916
See application file for complete search history.

(56) References Cited

U.S. PATENT DOCUMENTS

| 5,185,809 | A  |   | 2/1993  | Kennedy et al. |         |
|-----------|----|---|---------|----------------|---------|
| 5,195,519 | A  | * | 3/1993  | Angelsen       | 600/454 |
| 5,370,135 | A  | * | 12/1994 | Dullien        | 128/898 |
| 5,588,435 | A  |   | 12/1996 | Gueck et al.   |         |
| 5,605,155 | A  | * | 2/1997  | Chalana et al. | 600/443 |
| 5,795,296 | A  | * | 8/1998  | Pathak et al.  | 600/443 |
| 5,838,592 | A  |   | 11/1998 | Spratt         |         |
| 6,200,279 | B1 | * | 3/2001  | Paltieli       | 600/588 |
| 6,375,616 | B1 |   | 4/2002  | Berman et al.  |         |
| 6,669,653 | B2 | * | 12/2003 | Paltieli       | 600/588 |
| 7,087,022 | B2 | * | 8/2006  | Chalana et al. | 600/449 |
| 7,447,542 | B2 | * | 11/2008 | Calderon et al.| 600/546 |

(Continued)

*Primary Examiner*—Brian Casler
*Assistant Examiner*—Baisakhi Roy
(74) *Attorney, Agent, or Firm*—Dekel Patent Ltd.; David Klein

(57) ABSTRACT

A method for early detection of a pregnancy complication, including touching a position sensor to a point on a fetal presenting part of a fetus in a mother, and capturing a position of the position sensor, touching the position sensor to a set of points on the mother and capturing the position of the position sensor at each point, and detecting a pregnancy complication sign based upon a predefined criterion for said pregnancy complication. Methods and apparatus are provided for identifying the BPD pattern in an ultrasound image, for determining characteristics of body parts outside of a pelvic region, for BPD reconstruction and for an adapter for a position sensor are also described among other embodiments.

7 Claims, 21 Drawing Sheets

U.S. PATENT DOCUMENTS

2003/0114779 A1  6/2003  Paltieli
2006/0015036 A1* 1/2006  Paltieli ........................ 600/558
2008/0167581 A1* 7/2008  Paltieli ........................ 600/588
2008/0234581 A1* 9/2008  Paltieli et al. ................ 600/443

* cited by examiner

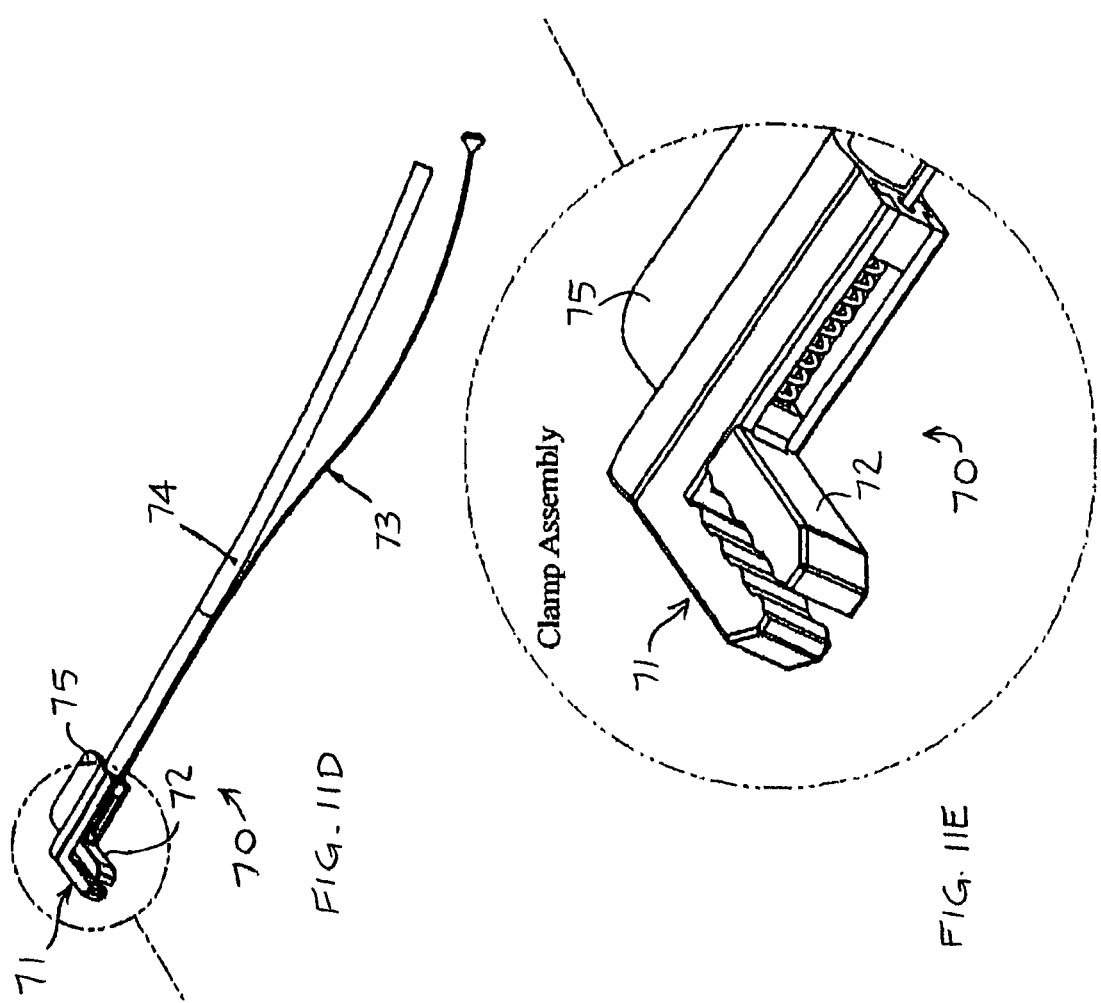

METHOD AND APPARATUS FOR MONITORING LABOR PARAMETER

FIELD OF THE INVENTION

The present invention relates to a method and apparatus for monitoring the progress of labor and labor parameters during childbirth.

BACKGROUND OF THE INVENTION

Normal labor is generally divided into three stages: the first stage begins with the onset of labor and ends when dilatation of the cervix is complete; the second stage begins at that point and ends with the complete birth of the baby; and this is followed by the third stage which ends with the delivery of the placenta. During labor it is common to use either an external ultrasonic system for recording the baby's heart rate, and an external system for detecting the mother's uterine contractions, or an electronic system to sense the baby's heart pulses by an electrode attached to the baby's head and the mother's contractions by a pressure catheter applied to the mother inside the uterus.

However, a number of other physiological conditions of the mother and baby during labor can also be monitored in order to determine the progress of labor. These additional conditions include: (1) effacement (the thinning out of the cervix that occurs before and during the first stage of labor); (2) cervical dilatation (the increase in size of the cervical opening); (3) position of the cervix (the relation of the cervix to the vaginal axis, normally the fetal head); (4) station (the level of a predetermined point of the fetal presenting part with reference to the mother's pelvis), (5) position of the head which describes the relationship of the head to the pelvis and (6) and presentation which describes the part of the fetus (such as brow, face or breech) at the cervical opening.

The more common determination of station is the distance between the tip of the fetal head and the ischial spines which can be palpable by the physician; but a more accurate determination of station is the distance between the bi-parietal diameter (BPD) of the fetal head and the mother's pelvic inlet.

The foregoing conditions are generally determined by a physical examination, e.g., by the insertion of a finger through the mother's vagina. However, the accuracy of such a "finger" examination is very subjective and depends to a great extent on the experience, judgment, and even finger size, of the physician. Other drawbacks in such a physical examination are that it can be done only at spaced intervals, it generally produces discomfort to the mother, and it involves a number of risks including contamination, infection, dislodgment of a fetal monitor, injury to the baby, etc. Failure to interpret the precise stage of the labor progress from the physical examination can result in injury or even death of the baby or of the mother.

Many devices have been proposed in the past for automatically monitoring these conditions. As examples, U.S. Pat. No. 4,476,871 proposes an elongated tube having electrodes spaced along its length to monitor cervical dilatation during labor; U.S. Pat. Nos. 4,942,882 and 5,135,006 propose a fetal monitor probe attached to the fetal head to monitor heart beat, which probe is calibrated to monitor progress of descent; U.S. Pat. No. 5,222,485 proposes an elongated inflatable sac to monitor the position of the fetus and the configuration of the cervix; and U.S. Pat. No. 5,406,961 proposes a pessary to monitor the configuration of the cervix. However, for one reason or another, none of the previously proposed devices has come into any widespread use, and the historical "finger" examination continues to be the one in common use to this day.

Recent studies (Sherer et al., Ultrasound Obstet Gynecol 2002 March; 19(3)):258-68) have demonstrated a high rate of error (75% and 65%) in transvaginal digital determination of fetal head position during active labor and the second stage of labor (respectively). The inaccurate assessment of the station or the position of the head also lead to decisions to use forceps or vacuum when the baby's head is too high in the birth canal, as well as delay in performing C-section when needed. In both cases the end result can be lethal to the fetus and highly damaging to the mother.

Moreover, the "digital (finger) test" can cause infections, and is forbidden in cases of early amniotic rupture. It also puts a heavy workload on the delivery room staff, particularly during peak periods. Furthermore, since the digital examination is intermittent, trends and sharp changes in the progress of labor are sometimes missed, again leading to potentially wrong decisions. Also, multiple digital examinations increase the risk of inflammation.

U.S. Pat. No. 6,200,279 to Paltieli, incorporated herein by reference in its entirety, describes improved methods and apparatus for monitoring the progress of labor. In one embodiment, the progress of labor is monitored by attaching a position sensor to a predetermined point on the mother's pelvic bones, monitoring the location of the position sensor in three-dimensional space relative to a reference, and monitoring the location of the fetal presenting part with respect to the predetermined point on the mother's pelvic bones. The location of the fetal presenting part may be indicated by a similar position sensor, or by imaging. Other conditions, such as effacement, cervical dilatation, and cervical position may also be monitored in a similar manner.

In U.S. Pat. No. 6,669,653, a continuation-in-part of U.S. Pat. No. 6,200,279, further embodiments are described. According to one aspect of U.S. Pat. No. 6,669,653, there is provided a method of monitoring the progress of labor in a mother during childbirth, comprising: attaching a position sensor to a predetermined point on the mother's pelvic bones; monitoring the location of the position sensor in three-dimensional space relative to a reference; monitoring the location of the fetal presenting part with respect to the predetermined point on the mother's pelvic bones to provide an indication of the progress of labor; and measuring the cervical dilation by attaching sensors to the cervix.

In another embodiment of U.S. Pat. No. 6,669,653, there is provided a method of non-continuous monitoring of the progress of labor in a mother during childbirth, comprising: using a probe or finger-mounted sensor to measure the fetal presenting part relative to a predetermined point on the mother's pelvic bone, and to measure the cervical dilation by touching the cervix in, for example, two points.

In another embodiment, the locations of the fetal presenting part and of the opposite sides of the end of the mother's uterine cervix may be monitored by position sensors attached to these respective elements. In a second described embodiment, the latter are monitored non-continuously using a hand held probe or finger-mounted sensor. In a third described embodiment, the latter are monitored by operating an ultrasonic transducer to image the mother's cervix and pelvic bones, and the fetal head, on a screen, and by using a position sensor on the ultrasonic transducer, and a marker for marking the screen, to locate the positions of these elements. A fourth embodiment is described utilizing at least two sensors, one of which is attached to a bony position on the pelvis to serve as the reference point, and the others may first be used to map the pelvis from outside of the body and to map the BPD plane by attaching it to the ultrasound probe, to map the ischial spines and ischial tuberosities from the inside and then to be attached to the cervix and fetal presenting part.

In a further embodiment of U.S. Pat. No. 6,669,653, position sensors may also be attached to, or position coordinates may be obtained of, the anterior superior iliac spine, the pubic symphysis, the scrum at 1-3 levels, the ischial spines and the ischial tuberosity, and such positions may be used for mapping the pelvic inlet outlet and midpelvis. Such mapping or pelvimetry may be helpful in determining whether the head of the baby is of suitable size for passage through the birth canal.

According to further features in U.S. Pat. No. 6,669,653, the cervical dilatation of the mother's cervix is continuously indicated by monitoring the positions of the position sensors applied to the opposite sides of the end of the cervix, and continuously displaying the spatial distance between them. The position of the fetal presenting part (e.g., fetal head) is also continuously indicated by monitoring and displaying their respective locations.

In another embodiment, the cervical dilatation of the mother's cervix and the position of the fetal presenting part or the BPD are monitored on a non-continuous basis by touching a probe or finger-mounted sensor to each side of the cervix and a pre-determined point or points on or connected to the fetal head.

According to further features in U.S. Pat. No. 6,669,653, the above conditions are computed and displayed in the form of units of distance (e.g., cm), and/or in the form of a graph, which may be called a partogram, showing the interrelation of the cervical dilatation and the descent of the fetal presenting part. Furthermore, such display may include an image of the fetus within the birth canal and the relation and orientation over time of the head to the pelvic inlet, outlet and midpelvis. FIG. 4A presents an illustration of a display of position of the presenting part in various stages of labor, in accordance with an embodiment of U.S. Pat. No. 6,669,653. Other methods to display such information may be used.

According to a further embodiment of U.S. Pat. No. 6,669,653, there is provided an apparatus for monitoring the progress of labor in a mother during childbirth, including: at least two sensors, one of which is attached to a bony position on the pelvis 8 to serve as the reference point, and another may first be used to map the pelvis from outside of the body, to map the BPD plane by attaching it to the ultrasound probe, to map the ischial spines and ischial tuberosities from the inside and then to be attached to the fetal presenting part, and may be attached to the sides of the cervix.

The output device is preferably a display, but could be a plotter, recorder, or other device for displaying, recording, and/or processing the data outputted by the computer Such a method and apparatus permits the progress of labor to be monitored in a manner which is either continuous or intermittent, which is less dependent for accuracy on the experience, judgment or finger size of the attendant in the conventional "finger examination", which subjects the mother to less discomfort, and which involves less risk of contamination, infection, dislodgment of a fetal monitor, or injury to or death of the baby or mother due to a wrong assessment of the fetal position or of labor progress. Moreover, this technique enables more precise monitoring of the critical condition, namely the changes in the spatial distance of the BPD of the baby's head with respect to the pelvic inlet.

SUMMARY OF THE INVENTION

The present invention seeks to provide different improvements and features heretofore not described in U.S. Pat. Nos. 6,200,279 or 6,669,653.

In one embodiment of the present invention, methods and apparatus are provided for early detection of pregnancy complications, such as but not limited to, preterm labor or threatened abortion, as is described more in detail hereinbelow.

In another embodiment of the present invention, a method is provided for identifying the BPD pattern in an ultrasound image, as is described more in detail hereinbelow.

Further features and advantages of the invention will be apparent from the description below.

BRIEF DESCRIPTION OF THE DRAWINGS

The invention is herein described, by way of example only, with reference to the accompanying drawings, wherein:

FIGS. 11D and 11E illustrate still another adapter for attaching the position sensor to the electrode, in accordance with still another embodiment of the present invention;

DETAILED DESCRIPTION OF THE INVENTION

In the following description, various aspects of the present invention will be described. For purposes of explanation, specific configurations and details are set forth in order to provide a thorough understanding of the present invention. However, it will also be appreciated by one skilled in the art that the present invention may be practiced without the specific details presented herein. Furthermore, well known features may be omitted or simplified in order not to obscure the present invention.

Figure 1:
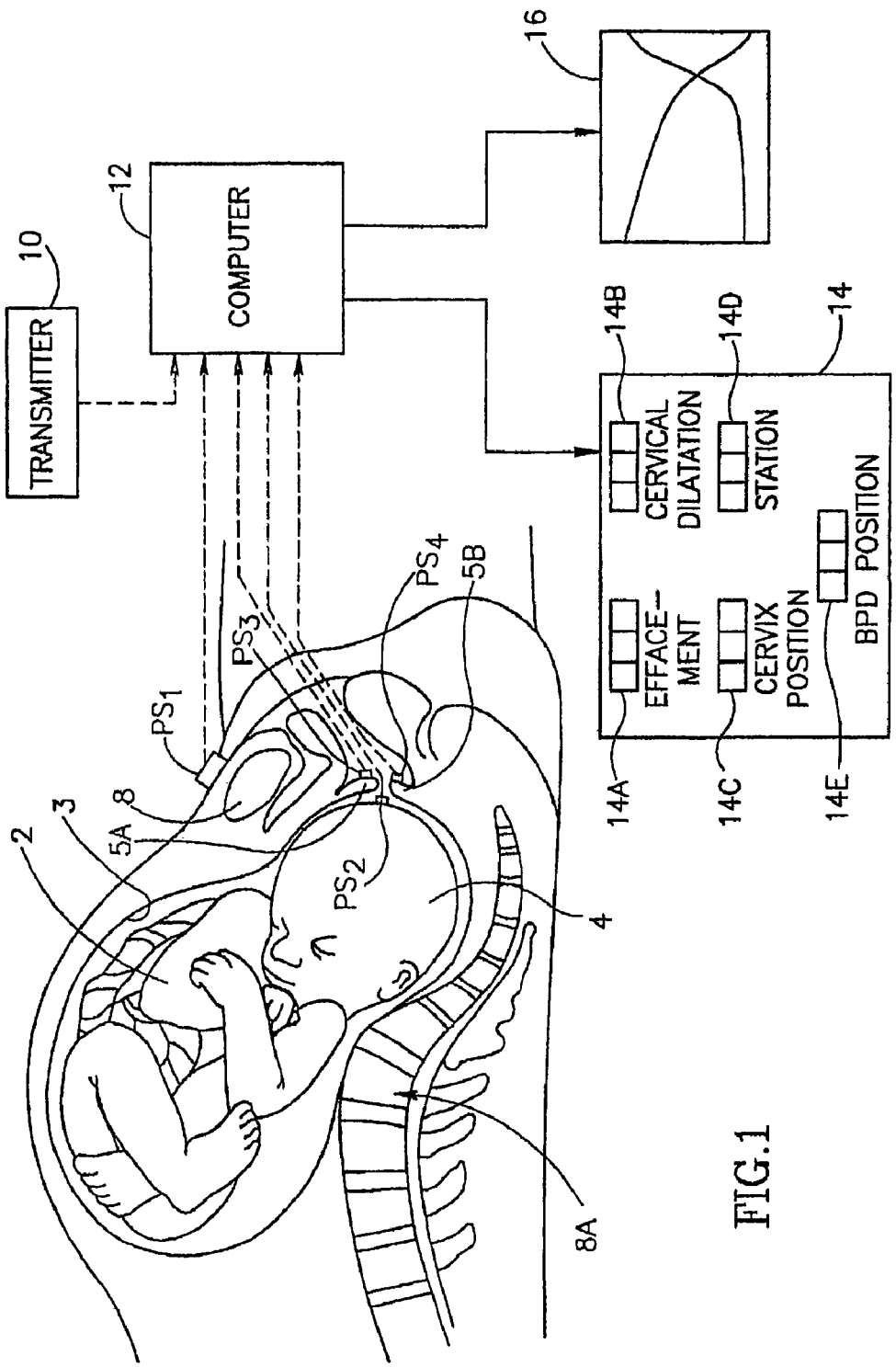
FIG. 1 is a block diagram illustrating one embodiment of a system constructed in accordance with the present invention.

Referring to FIG. 1, FIG. 1 schematically illustrates an example of a mother's womb during labor and a system for monitoring the process. A computer 12 (which may be, for example, a personal computer, a workstation, a dedicated device including a "computer on a chip", etc), inter alia, outputs displays, such as displays 14 or 16, to, for example, a monitor. Displays other than those shown may be used. Computer 12 is operatively connected to, for example, a transmitter 10 and sensors PS. Transmitter 10 need not be used. Computer 12 typically includes appropriate software and one or more appropriate processors for processing data from the sensors described herein, such processors being well known to those skilled in the art. FIG. 1 depicts the fetus 2 in its normal position within the uterus 3 wherein the fetal head 4 is downwardly oriented in preparation for delivery via the cervix 5 of the uterus. The cervix 5 is dilated and effaced in preparation for passage of the fetus via the cervical canal and the vaginal cavity. The various stages of descent of the fetal head during delivery may be measured, for example, in relation to the ischial spines or the pelvic inlet 8a of the pelvic bones 8.

The progress of labor is monitored by, for example, a set of position sensors attached to the fetal head and to the various parts of the mother's womb and pelvis, as follows: a first position sensor $PS_1$, may be attached to, for example, one of the pelvic bones 8 as a reference point from the ischial spines and the pelvic inlet 8a; a second position sensor $PS_2$ may be attached to the fetal head 4 (or other typically presenting part of the unborn baby if not the fetal head); and third and fourth position sensors $PS_3$ and $PS_4$ may be attached to, for example, the opposite sides of the two ends of the external opening of the uterine cervix 5A and 5B. Attachment positions varying from those shown may be used.

Suitable position sensors include, but are not limited to, positional tracker sensors, such as the 3D positional trackers manufactured by Ascension Technology Corporation, Burlington, Vt., US, under the model names MicroBIRD and PcBIRD or PciBIRD. MicroBIRD sensors are quite small (1.8 mm diameter×8.5 mm length) whereas PcBIRD or PciBIRD are larger (18 mm×8 mm×8 mm).

In alternative embodiments, position sensor PS2 may be attached to or made part of (e.g., with suitable adapters described hereinbelow), for example, a fetal scalp electrode as are known in the art and as are commonly used in monitoring fetal life signs. For example, a position detection sensor PS2 may be attached to or made part of a Copeland fetal scalp electrode (Sturgicraft, England) that attaches to the fetus with a hook, or to a fetal scalp electrode that attaches to a fetal presenting part with, for example, a screw, spring or spiral, etc. Other fetal electrodes or sensors may be used, for example, fetal spiral electrodes. Suitable fetal spiral electrodes include without limitation, the Corometrics E9007JC Qwik Connect Plus fetal spiral electrode (K792669) or the Hewlett Packard/Philips 15133E spiral fetal scalp electrode. These are safe, easy to use scalp electrodes for the attachment of sensors to the fetal head tip.

In other embodiments, position sensor PS2 may be attached to the fetal presenting part via other methods, such as with a suction cup, tape or other adhesive, etc.

A computer or monitor 12 can track movements of the pelvis, and thus can monitor the spatial position of the entire pelvis, particularly the pelvic inlet, outlet and midpelvis.

In certain embodiments, the position sensors $PS_1$-$PS_4$ may be fixed in any suitable manner (e.g., by clips, suction cups, or other adhesives, etc.) to its respective surface. Each is typically capable of sensing its precise position and orientation in three-dimensional space with respect to a reference, as described in greater detail below. The position sensor may also be carried at one end of a rigid rod or object or other support which is clipped at its other end to the respective surface.

In an alternate embodiment of the present invention, the progress of labor is monitored on a non-continuous basis by a position sensor mounted on a hand held probe or on a thimble or other finger mount. In one embodiment, a user's finger is used to manipulate the probe, and the finger has mounted on it a position sensor. The probe is touched to various points on the fetus and mother. The probe may also be, for example, mounted on a rod or other rigid object.

Figure 11:
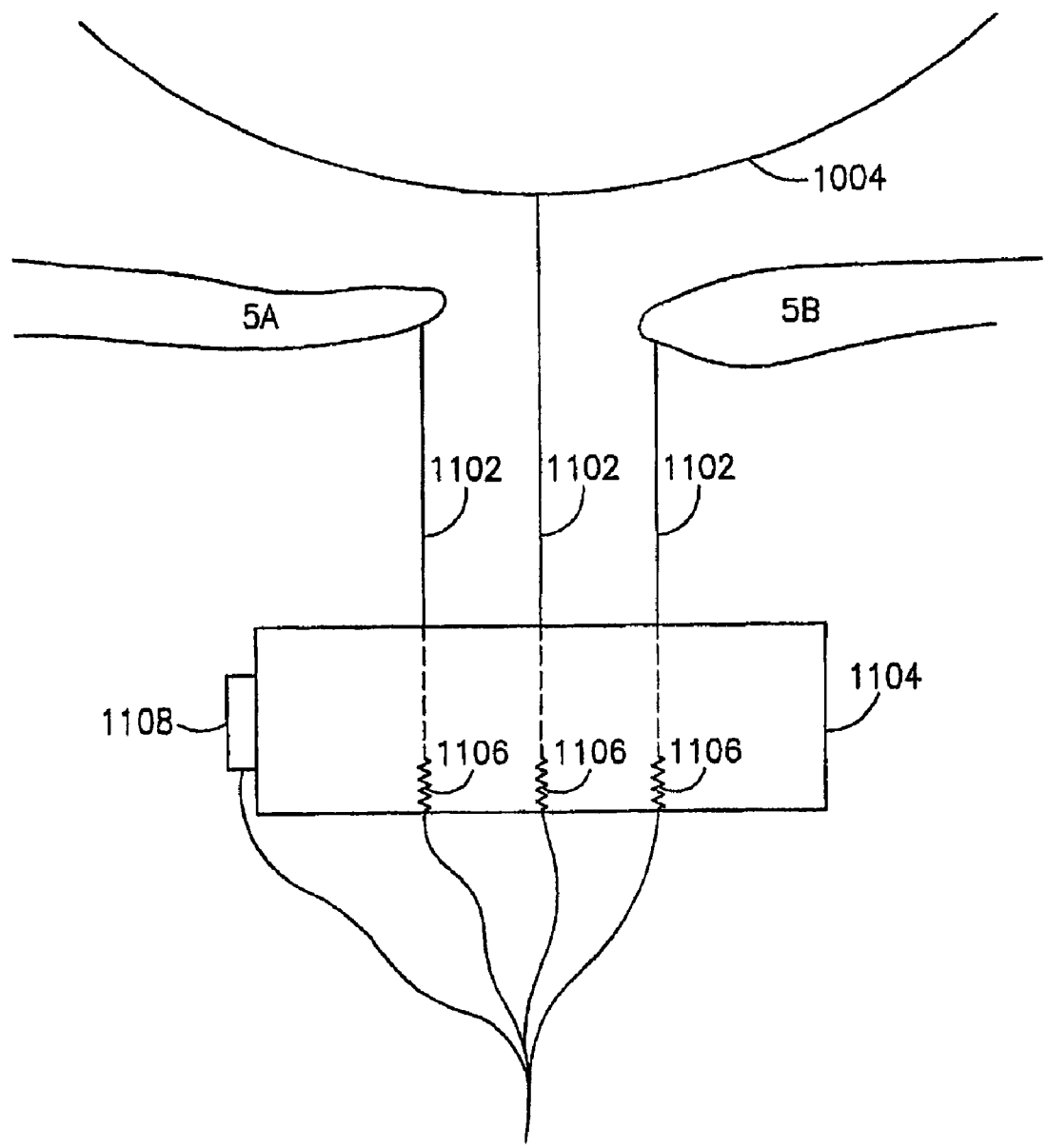
FIG. 11 illustrates rigid members that can be attached to the cervix and fetal presenting part in accordance with an embodiment of the present invention.
Figure 11A:
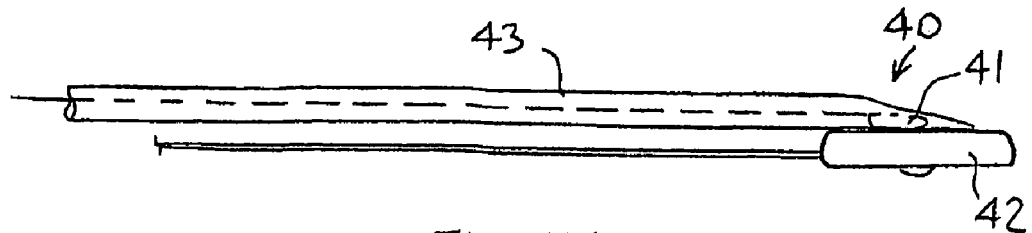
FIG. 11A illustrates an adapter for attaching a position sensor to an electrode or sensor, constructed and operative in accordance with an embodiment of the present invention.

Reference is now made to FIG. 11A, which illustrates an adapter 40 for attaching a position sensor 41 to an attachment point, surface or device, such as but not limited to, an anatomical landmark, constructed and operative in accordance with an embodiment of the present invention.

Adapter 40 may include a sleeve 43, into which the position sensor 41 is inserted. The sleeve 43 may be constructed, without limitation, from a medical, biocompatible polyethylene material. The sleeve 43 may be sterile and a distal portion 44 thereof may be attached to an attachment device 42, such as but not limited to, by means of medical adhesive, sonic bonding, mechanical fasteners (e.g., screws) and the like. Attachment device 42 may include, without limitation, a rigid or flexible body (e.g., made of a medically safe plastic) which may be attached to tissue or any portion of a body, or may comprise an electrode or sensor (the terms being used interchangeably throughout the specification and claims), such as a scalp electrode which may be attached to a fetal scalp or to a portion of the cervix. The position sensor 41 may be inserted into the sleeve 43, and may be held there simply by friction or optionally with adhesive or other bonding or attachment means.

Alternatively, position sensor 41 may be attached to sleeve 43 or directly to the attachment point or device. As another alternative, position sensor 41 may be attached to a rigid mechanical connection 45, which is assembled with (e.g., inserted in) the sleeve 43 or attached directly to the fetal head and/or a portion of the cervix. In such an alternative, the position sensor 41 is remote to the attachment point.

Figure 11B:
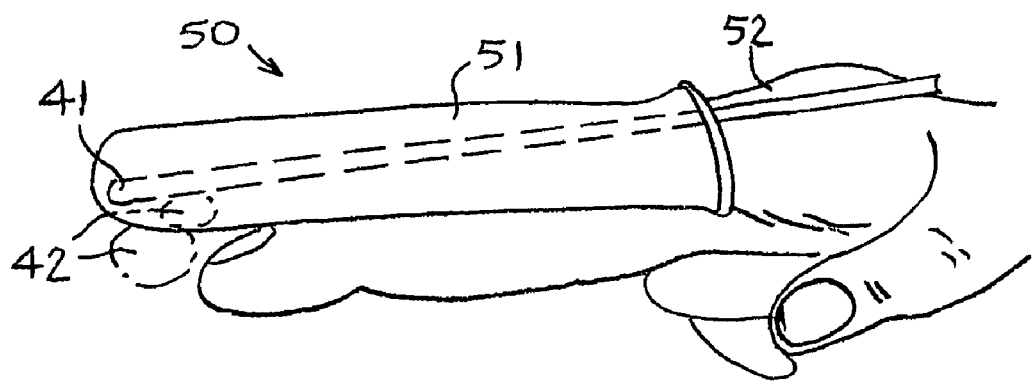
FIG. 11B illustrates another adapter for attaching the position sensor to the electrode, in accordance with another embodiment of the present invention.

Reference is now made to FIG. 11B, which illustrates another adapter 50 for attaching position sensor 41, in accordance with another embodiment of the present invention. In this embodiment, adapter 50 includes an elastic, stretchable sleeve 51, e.g., a condom, into which the position sensor 41 is inserted. This embodiment is particularly useful for manual manipulation, by sticking a finger 52 of a user into sleeve 51 together with the sensor 41. The user can then touch any anatomical landmark with great dexterity. An attachment device (e.g., electrode 42) may optionally be inside sleeve 51.

Proper orientation of the position sensor with respect to the sleeve and/or the attachment device/point (which may involve six degrees of freedom in 3D space) may be established by means of geometric keying. "Geometric keying" may include fashioning the position sensor with a certain geometric shape (e.g., triangular, trapezoidal, etc.) and fashioning the attachment place in the sleeve and/or the attachment device/point with a complimentary geometric shape such that the two parts fit together like a jigsaw puzzle and positively and unequivocally establish the proper spatial and rotational orientation of the sensor.

Figure 11C:
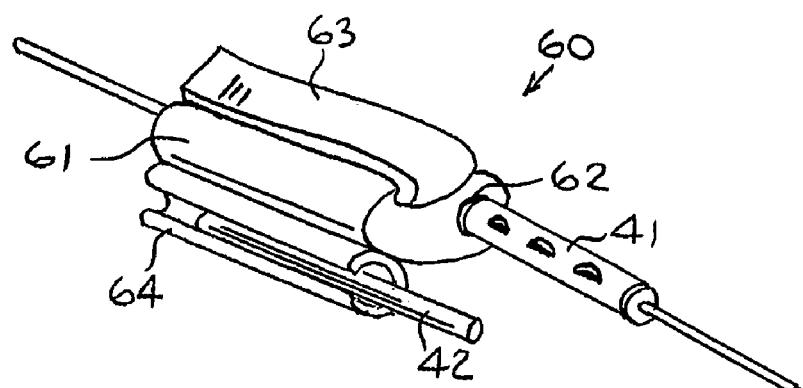
FIG. 11C illustrates yet another adapter for attaching the position sensor to the electrode, in accordance with yet another embodiment of the present invention.

Reference is now made to FIG. 11C, which illustrates another adapter 60 for attaching position sensor 41, in accordance with yet another embodiment of the present invention. In this embodiment, adapter 60 includes a receptacle 61 with a recess 62 into which the sleeve 43 (with position sensor 41) may be inserted. The receptacle 61 may be considered a rigid sleeve and may be constructed of molded plastic, for example. A releasing lever 63 may be provided that the position sensor 41 engages when inserted in recess 62. The releasing lever 63 may be lifted or otherwise moved to release the position sensor 41, permitting its removal from receptacle 61. Adapter 60 may further include an attachment member 64 to which an electrode (sensor) 42 may be attached. For example, attachment member 64 may include a resilient arm (e.g., a resilient cylinder with a longitudinal slit) into which electrode (sensor) 42 may be snugly pressed.

Reference is now made to FIGS. 11D and 11E, which illustrate another adapter 70 for attaching position sensor 41, in accordance with still another embodiment of the present invention. In this embodiment, adapter 70 includes a clamp 71 with jaws 72. The jaws 72 may be actuated (i.e., opened and closed) by a drawstring 73 attached thereto. A sleeve or tube 74 may be attached to adapter 70 into which the position sensor 41 may be inserted. A finger receptacle 75 may be provided on the adapter body for placing therein a finger of a user (not shown). Adapter 70 may be particularly useful for clapping to a cervix, although the embodiment in not limited to this application and may be used in other applications as well.

It is noted that any of the above adapters and features thereof may be combined with one another in any combination.

Figure 10A:
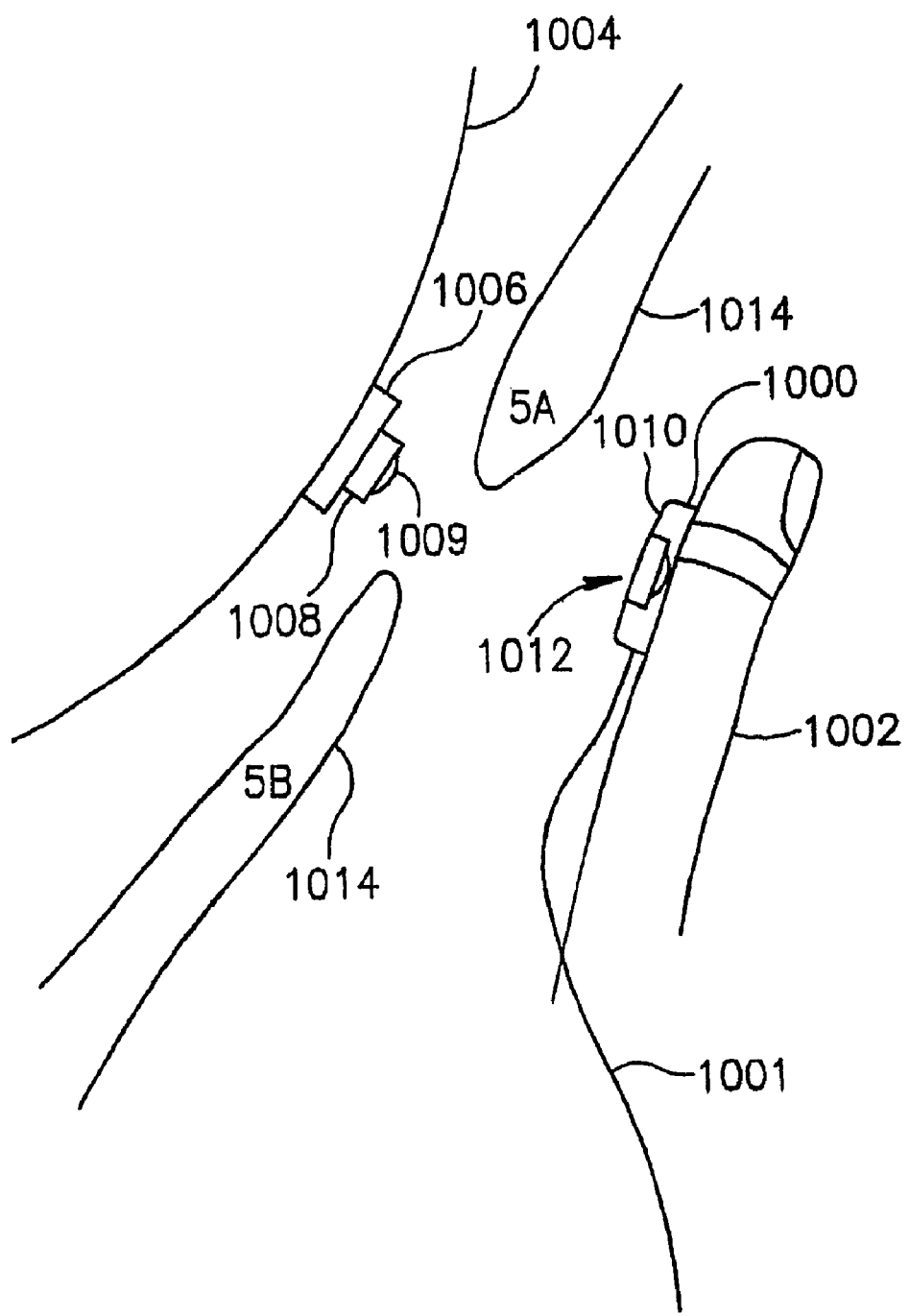
FIG. 10A illustrates a finger mounted sensor in accordance with an embodiment of the present invention.

Reference is now made to FIG. 10A which illustrates a schematic diagram of a position probe or finger-mounted sensor 1000 in accordance with an embodiment of the present invention. Position probe or finger mounted sensor 1000 in the shape of, for example, a thimble, may fit over the distal end of a finger 1002 of the doctor or medical practitioner performing an examination. Other shapes and fits such as a ring or glove for holding such sensor are also possible. A lead or wire 1001 operably connects finger mounted sensor to a computer, processor or fetal monitoring station. Alternatively, the operable connection can be over a wireless electronic data link. Sensor 1000 may operate similar to and may be used and incorporated into systems in a manner similar to probes PS discussed herein.

FIG. 10A also depicts fetal presenting part 1004 such as a head or other part to which has been attached a fetal scalp orientation guide 1006. Fetal scalp orientation guide 1006 may include appropriate electrodes, wires, or transmission devices (for, for example, transmitting heart rate information), or may not. Fetal scalp orientation guide 1006 may be fixed in any suitable manner (e.g., by clips, suction cups, or other adhesives, etc.) to its surface. Fetal scalp orientation guide 1006 may be attached to, may include, or may be made part of, for example, a fetal scalp electrode commonly used in monitoring fetal life signs; alternately fetal scalp orientation guide 1006 may not be associated with such devices. Fetal scalp orientation guide 1006 typically provides a reference or affixation point for contact with a position probe, and also provides an orientation guide for the position probe, by, typically, providing a key part or shape that forces, on appropriate contact with the position probe, the position probe (which includes a matching key part) to be oriented in a certain way with respect to the fetal scalp orientation guide 1006. Scalp orientation guide 1006 is affixed to the fetus in an appropriate manner.

The distal end 1010 of finger mounted sensor 1000 may be fitted with one or more typically asymmetrically shaped protrusions 1012 that fits and matches the form of one or more indentation(s) 1009 located typically on the outward facing side 1008 of the fetal scalp orientation guide 1006. Indentation(s) 1009 and protrusions 1012 each form a key part which matches the other part. The location of the protrusion(s) 1012 and indentation(s) 1009 may in other embodiments be alternated between the distal end 1010 of finger mounted sensor 1000 and the outward facing side 1008 of the fetal scalp orientation guide 1006. The shape and number of the protrusion(s) 1012 and indentation(s) may vary from as shown. The "protrusions" or key part may not extend from the surface of the electrodes; for example the protrusions may be indentations allowing for a corresponding key-portion to be inserted or matched. Wires need not be used, and the position probes may operate according to wireless methods as discussed below.

In one embodiment of the present invention, in use, the probe or finger-mounted sensor 1000 may be touched to, for example, the fetal head 1004 (or other presenting part of the unborn baby) and to a set of points (wherein set may include one element) on the mother. Typically, the sensor 1000 is touched to each side of the external opening of the uterine cervix 1014, but other parts of the mother may be used. Each side of the external opening of the uterine cervix 1014 may include key devices or guides for providing a reference or affixation point and orientation point, but typically no such device is needed on the mother. If such devices are used, they may be similar in shape to the guide 1006.

In certain embodiments, the sensor may be touch-sensitive so that the touch of the sensor such as finger mounted sensor 1000 to the fetal presenting point 1004 or cervix triggers the calculation of the position of such points. In other embodiments, the examining physician may contact the finger mounted sensor 1000 with the designated point such as the fetal head, and may initiate position capture by indicating to a computer or monitoring device. For example, the user may click a mouse or operate a keyboard, foot pad or other switch which is operably connected to such position sensor to provide a user indication and to trigger the calculation of the position of the respective points. Reference or affixation points other than those shown may be used. The calculation of the relative position of the touched fetal presenting point 1004 relative to, for example, the opposite ends of the mother's uterine cervix 5A and 5B (or to other points) may permit the calculation of the progress of labor.

In certain embodiments, it may be desirable to collect more information than the touch of a finger-mounted sensor 1000 to a point on fetal presenting part 1004 provides to, for example, establish a required accuracy of orientation of the touched spot relative to the pelvic bones. Thus, in order to calculate the position of the fetal presenting part, it may be desirable to fix the orientation of the touch of the sensor 1000 to the fetal presenting part 1004.

Figure 10B:
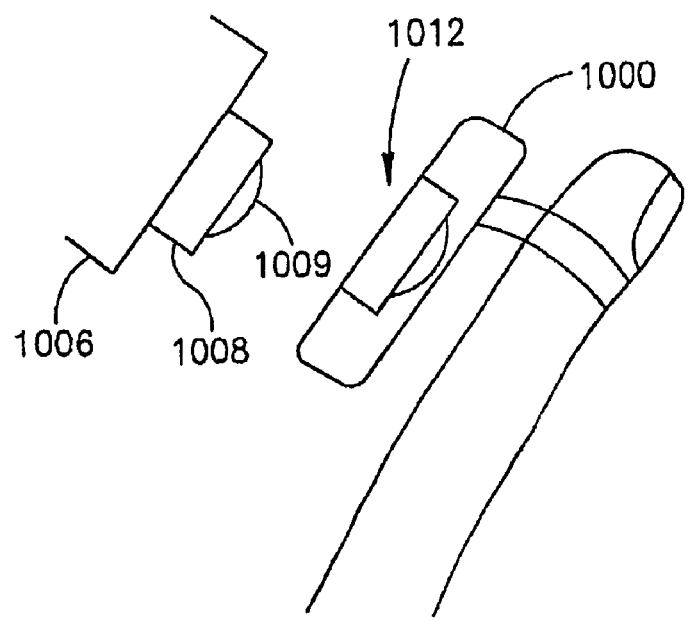
FIG. 10B illustrates a close up view of an asymmetrical indentation from a finger mounted sensor and a corresponding protrusion on a sensor attached to the fetal head in accordance with an embodiment of the present invention.

Reference is made to FIG. 10B which illustrates a close up view of an asymmetrical indentation protrusion(s) 1012 on a finger mounted sensor 1000 and a corresponding protrusion 1008 on a fetal scalp orientation guide 1006 in accordance with an embodiment of the present invention. Protrusions 1012 and 1008 typically provide a key system (fetal key and position key), when in contact, to fix their relative positions and orientations. A fixed orientation of the touch of the sensor 1000 to the fetal scalp orientation guide 1006 may be achieved by, for example, requiring that at the time of the calculation of the position of the sensor 1000 (e.g., the time of the click of the mouse as described above) protrusion(s) 1012 at the distal end 1010 of sensor 1000 is fitted onto the indentation(s) 1009 on the outward facing side of fetal scalp orientation guide 1006. Typically, the protrusions require that when the sensor 1000 and orientation guide 1006 are in full contact, they have a specific relative orientation to each other.

Alternatively, the orientation of the touch of sensor 1000 on fetal presenting part 1004 may be determined by, for example, touching several (typically three, although other numbers may be used) designated points on fetal presenting part 1004 or on fetal scalp orientation guide 1006. Such designated points could be, for example, any of three anatomical landmarks on the fetal head, such as the anterior and/or posterior fontanels, or three stickers or markers attached to the fetal presenting part 1004.

Figure 10C:
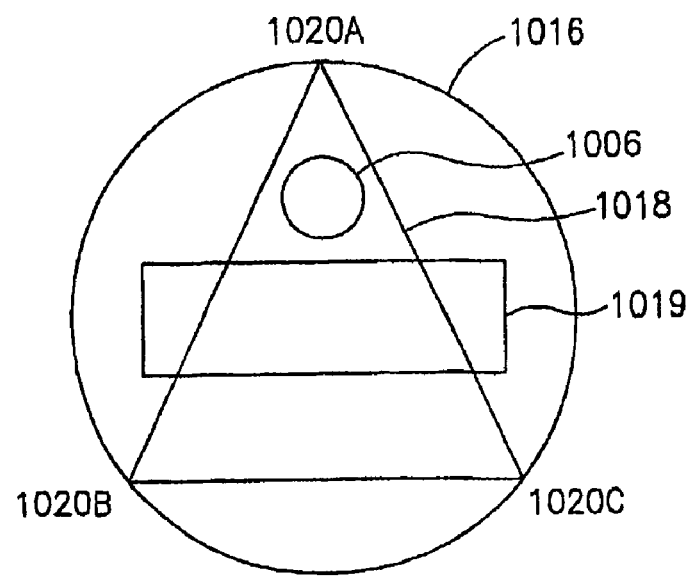
FIG. 10C illustrates an asymmetrically shaped cover that may be attached to a fetal sensor in accordance with an embodiment of the present invention.

Reference is made to FIG. 10C which illustrates a cap or covering that may be attached to fetal scalp orientation guide 1006 onto which is etched or attached an asymmetrically shaped form 1018 in accordance with an embodiment of the present invention. Other suitable forms, markings or shapes may be used. Establishing the orientation of the touch of sensor 1000 relative to fetal presenting part 1004 may be achieved by, for example, touching sensor 1000 to several (typically three, although other numbers may be used) points on asymmetrically shaped form 1018. Such three points can be in the form of, for example, a non-isosceles triangle of points 1020A, 1020B and 1020C which may be affixed or etched into fetal scalp orientation guide 1006. Other shapes can be used. In certain embodiments the cap may be omitted. In certain embodiments, asymmetrically shaped form 1018 can be etched into or attached directly onto fetal scalp orientation guide 1006 or onto other sensors attached to the fetus.

In other embodiments, a first end of several (typically three, although other numbers may be used) rigid members of known length can be attached to each of the two ends of the cervix 5A and 5B and the fetal presenting part 1004. A second end of each of such rigid members may be attached to, for example, a position sensor. Position and orientation of the cervix or the fetal presenting part cause the position of the sensors to change. In an alternative embodiment, the second end of such rigid members may be rotatably and moveably connected to a receptacle located outside of the body. Reference is hereby made to FIG. 11 which illustrates rigid members 1102, the first ends of which can be attached to, for example, the cervix 5A and 5B and fetal presenting part 1004 in accordance with an embodiment of the present invention. Other suitable attachment points, and other numbers of members, may be used. The second ends of such rigid members 1102 are movably inserted into, for example, a receptacle 1104 which measures the movement and orientation of such members 1102. Such movement of the members 1102 reflects the dilation and effacement of the cervix 5A and 5B and the station and position of the fetal presenting part 1004, and may recorded by, for example, an electronic, mechanical or optical reader located within receptacle 1104 and attached to each of the rigid members 1102. Receptacle 1104 may also have a position sensor as a reference point of the orientation of receptacle 1104 so that the position of rigid members is known relative to the position or receptacle 1104.

Position sensors may be, for example, magnetic, ultrasonic, mechanical (e.g., multi-articulated arm, balloon based sensor, scissors-configuration based sensor and others), inertial, optic, gyroscopic, accelerometer, potentiometer based sensor, radio frequency (RF) based sensor, or other known position sensors. Many types of position sensors are known for this purpose. In the illustrated example, position sensors $PS_1$-$PS_4$ and sensor 1000 are of the magnetic field type as described, for example, in U.S. Pat. No. 4,945,305 to Blood. Other position sensors and methods of computing positions from sensors may be used. The position sensors PS or sensor 1000 may, for example, output signals, when triggered by, for example a transmitter 10 (FIG. 1), enabling the precise position of the sensor to be computed by a computer 12 (FIG. 1) connected to receive the outputs of the position sensors as well as the signals transmitted by the transmitter 10. Computer 12 may compute the precise position and orientation of each sensor 1000 or sensor $PS_1$-$PS_4$, and from these computations, create and control displays for example those shown as 14 (FIG. 1) and 16 (FIG. 1), for displaying various physiological conditions of the mother and baby during labor, particularly the following (other conditions or sets of conditions may be presented):

1. Effacement 14A: This is the process of thinning out the cervix that takes place before and during the first stage of labor. The cervix is thinned by retraction in order to allow more room for the birth process. Effacement may be expressed as a percent, from zero percent (uneffaced) to one hundred percent (cervix less than about 0.25 cm thick). In the system illustrated in FIG. 1, effacement is computed and displayed at 14*a* as the spatial distance between position sensor $PS_2$ attached to the fetal head and the middle point on the line connecting the two position sensors $PS_3$, $PS_4$ attached to the ends of the uterine cervix 5. Positions of sensor 1000 at various points may also be used for such calculations. Other methods of defining or presenting effacement may be used.

2. Cervical dilatation 14B: This is the enlargement of the cervical opening. It is considered to be fully dilated when its diameter measures 10 cm since the fetal head of a term-sized infant usually can pass through a cervical opening of that diameter. In the system illustrated in FIG. 1, the cervical dilatation is computed and displayed at 14*b* as the spatial distance between the two position sensors $PS_3$, $PS_4$, attached to the opposite sides of the uterine cervix 5. The position of sensor 1000 at suitable points may also be used for such calculations. Other methods of defining or presenting cervical dilatation may be used.

3. Position of the cervix 14C: This is the forward-backward inclination of the cervix. In this case it is measured as the orientation of the central axis of the cervix, which is the line connecting the position sensor $PS_2$, attached to the presenting part of the fetus, and the middle point on the line connecting the two position sensors $PS_3$, $PS_4$ attached to the opposite sides of the cervix. An initial orientation of that cervical axis may be taken at the beginning of labor, and the progress of the cervical position is indicated as the relative angle between the cervical axes at any given time to the angle of initial orientation. The physician may designate any angular range as, for example, "forward", or "middle", or "backward". Alternatively, the cervical position may be indicated as the distance between the symphys pubis, as determined by position sensor $PS_1$, and the middle point of the line connecting the two position sensors $PS_3$, PS4 attached to the opposite sides of the cervix. Other methods of defining or presenting cervix position may be used. For example, the position of sensor 1000 at various points may also be used.

Figure 7:
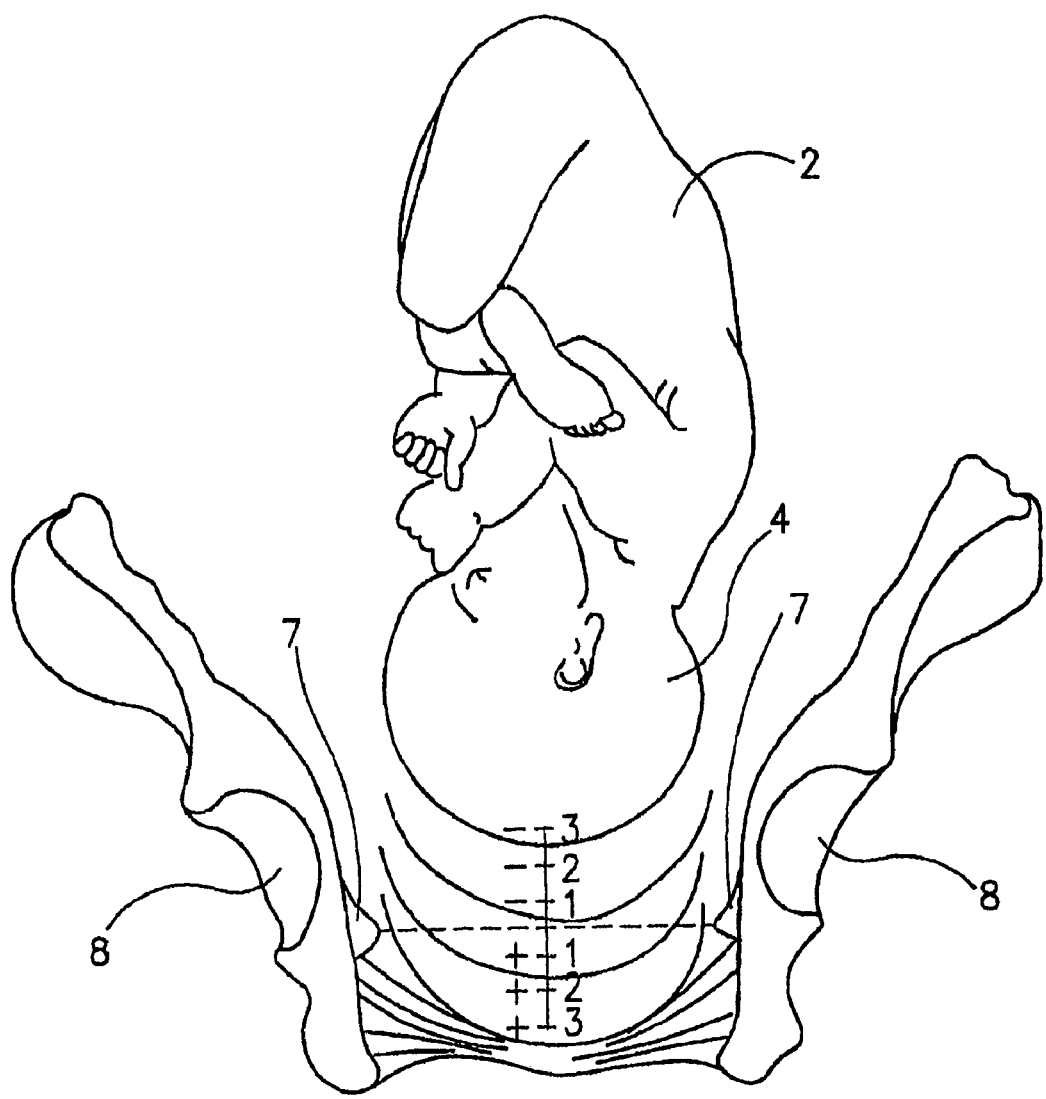
FIG. 7 illustrates a display produced by the system of FIG. 5 during the descent of the fetal head, according to an embodiment of the invention.
Figure 8:
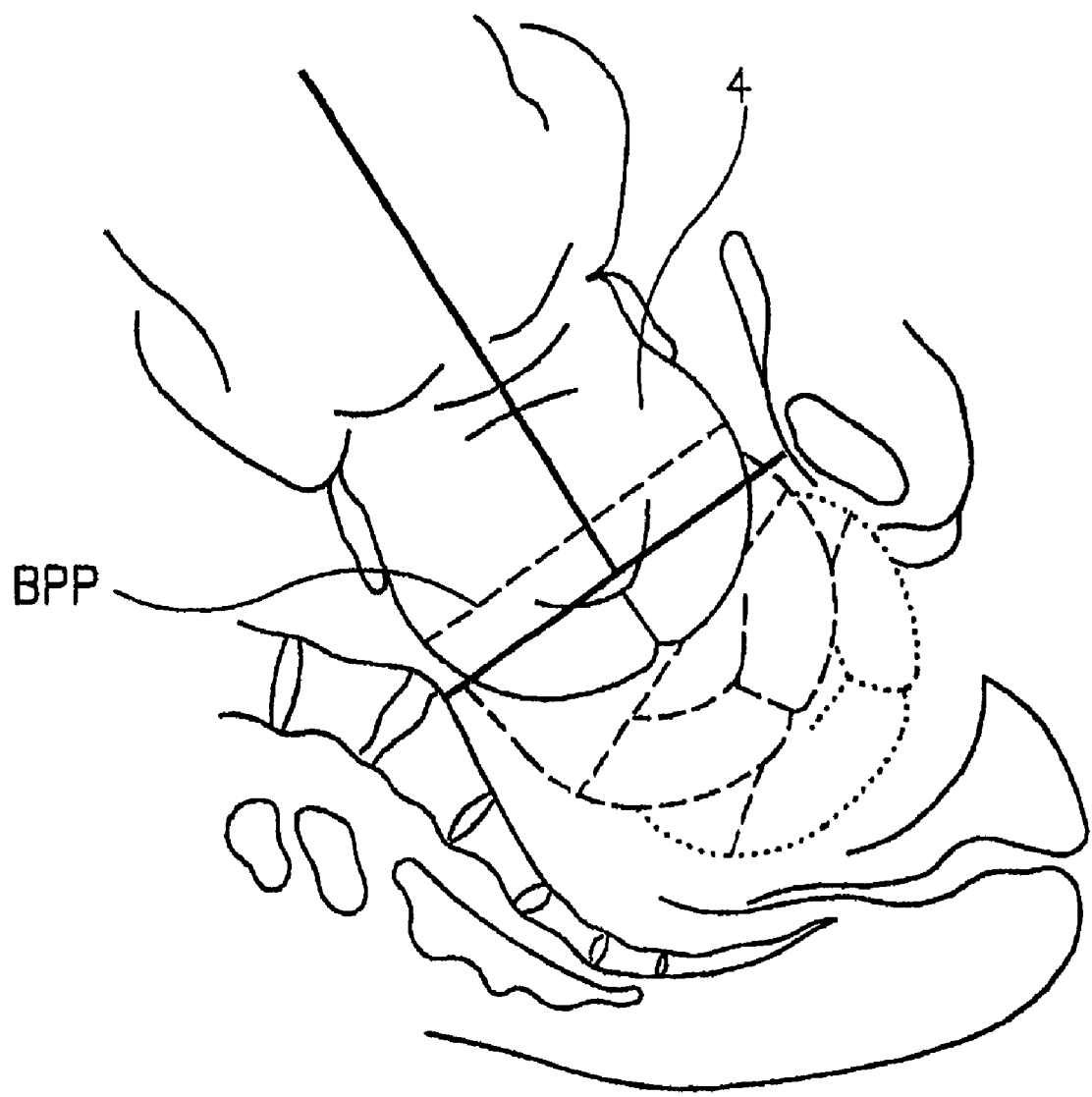
FIG. 8 illustrates how the monitored data may be processed to display the changes in the spatial distance of the BPD of the baby's head with respect to the mother's pelvic inlet, according to an embodiment of the invention.

4. Station 14D: This is the position of the fetal head (or other presenting part) with respect to a predetermined point of the mother's pelvis. As indicated earlier, the conventional station is the distance between the tip of the fetal head and the ischial spines. In one embodiment, a more accurate way of measuring the station may be used: to measure the distance between the BPD and the pelvic inlet. In the systems illustrated herein, the station may be computed and displayed in the conventional manner, based on the distance between the tip of the fetal head and the ischial spines as illustrated in FIG. 7, or in the more accurate manner based on the spatial distance of the BPD to the pelvic inlet as illustrated in FIG. 8. Other methods of defining or presenting such position may be used.

5. Position of the head which describes the relationship of the head to the pelvis, and presentation which describes the part of the fetus (such as brow, face or breech) at the cervical opening. Other methods of defining or presenting such position may be used.

6. Pelvimetry: This is the mapping or calculating of the area and shape of the pelvic inlet and pelvic outlet and midpelvis as are known in the art. A purpose of such mapping may be to determine whether the area of the pelvic inlet, outlet and midpelvis is suitable for passage of the baby. Other methods of defining or presenting such areas and shapes may be used.

In addition the invention may be used for mapping a body part outside of the pelvic region, such as (without limitation) by external sensors and extrapolation or other algorithms.

Figure 2:
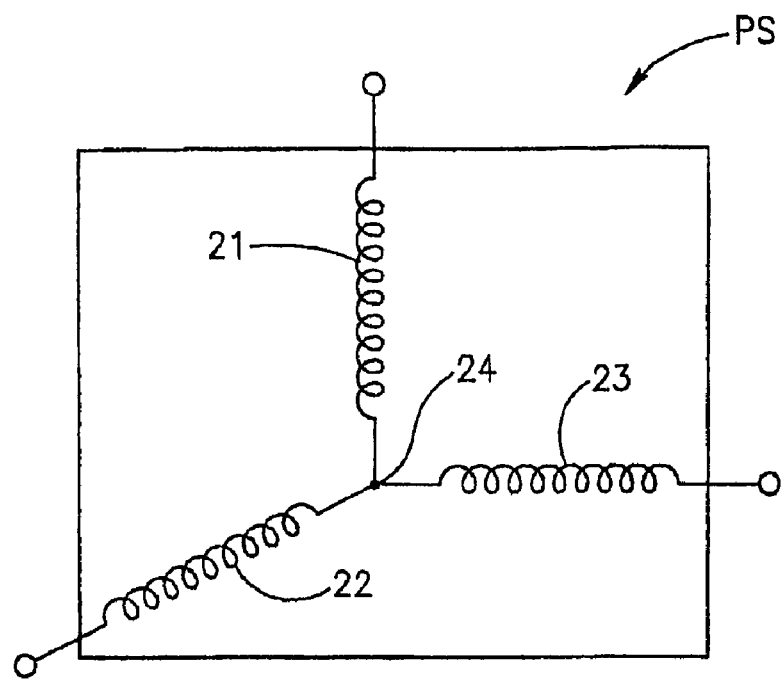
FIG. 2 illustrates one of the position sensors in the system of FIG. 1, according to an embodiment of the invention.

The present invention may in certain embodiments provide a method of obtaining increased accuracy of pelvimetry. Such pelvimetry may be obtained by initially attaching or touching a sensor to some or all of the bony pelvis and the spine, and to some or all of the following spots in the mapping stage: the anterior superior iliac spines, pubic symphysis, the sacrum at 1-3 levels as may be measured externally or through the vagina, the ischial spines and the ischial tuberosity. Other measurement areas or sets of measurement areas may be used. Pelvimetry may be performed by embodiments of the present invention during active labor, before the onset of such labor, or at any other time The position sensors $PS_1$-$PS_4$ or 1000 may be of various known types. FIG. 2 schematically illustrates one of such position sensors PS or 1000. It includes a, for example, triangular array of several (typically three, although other numbers may be used) spaced-apart magnetic coils 21, 22, 23, all at precisely known distances from the center point 24 of the position sensor. Thus, by determining the positions and orientations of the three coils 21-23 with respect to a reference, the precise location of the center point 24 of the position sensor PS or 1000 can be determined with respect to that reference.

Figure 3:
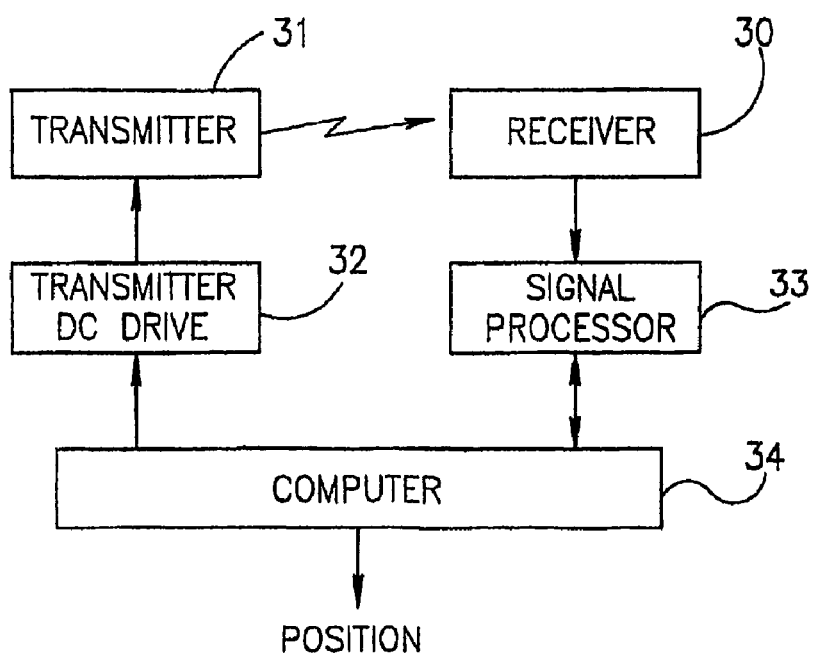
FIG. 3 is a block diagram of one type of position sensor system that may be used, according to an embodiment of the invention.

An example of a position sensor system which could be used with various embodiments is that described in U.S. Pat. No. 4,945,305 to Blood. Such a system, illustrated in the block diagram of FIG. 3, is capable of precisely measuring the position (location and orientation) in six degrees of freedom of receiving antenna 30 with respect to transmitting antenna 31 utilizing pulsed DC magnetic signals. The transmitting and receiving components consist of two or more transmitting antennas of known locations and orientation with respect to each other. The transmitting antennas 31 are driven one at a time (by a pulsed, direct current signal) from a DC drive circuit 32. The receiving antenna 30 measures the transmitted direct current magnetic fields and the earth magnetic field in a signal processing circuit 33 and feeds this information to a computer 34 which thereby determines the position of the receiver antenna 30. The computational processes taught by Blood may be used with various embodiments of the system and method of the present invention, and, for example, may be embodied in the computer 12 and/or software within the computer 12. Other methods of computation may be used.

Further details of the construction and operation of such a position sensor system are set forth in U.S. Pat. No. 4,945, 305, which is hereby incorporated by reference in its entirety. Other magnetic field systems which may be used with embodiments of the present invention may be, for example, based on AC fields, such as described in the patents set forth in the discussion of the prior art in the Blood patent.

Other position sensing systems that could be used for the position sensors $PS_1$-$PS_4$ or 1000 are, for example, those produced by Polhemus Inc. or by Ascension Technology Corporation, both of Burlington, Vt., USA. In such systems, for example three mutually perpendicular magnetic fields are transmitted in sequence, and for example three mutually perpendicular directional coils are employed to detect the several magnetic fields. A computer is employed to compute the spatial position and orientation of the combined coils.

A still further position sensing system that could be used is that produced by Adaptive Optics Associates, Inc., of Cambridge, Mass., USA. This includes multiple light sources attached to the object whose position and orientation is to be detected, and a multiplicity of cameras positioned in known spatial locations to detect the light emitted by the light sources. A computer combines all the data and computes the position and orientation of the object.

Yet another position sensor system that could be used is that of Science Accessories Corporation of New Haven, Conn., USA. It includes an ultrasound source attached to the point on the object whose position is to be detected, and a multiplicity of microphones positioned in known spatial locations to detect the sound emitted by the ultrasound source. A computer combines the data and computes the position of the object. By attaching multiple spaced-apart ultrasound emitters of the object, its orientation can also be computed by combining the position data of each of the emitters.

In one embodiment, the position sensors are of the wireless type so as to minimize interference with the birth process. In some cases it may be advantageous to use a mechanical positioning system based on robotic arms physically connected to the tracked objects and equipped with mechanical sensors at the joints (e.g., rotary encoders) which enable precise spatial location of the tracked objects.

Computer 12 (FIG. 1) which receives data corresponding to the positions of the position sensors $PS_1$-$PS_4$ (or, in one embodiment, sensor 1000, FIG. 10), processes this data to provide the type of display that may be desired. Computer 12 may include software, memory, mass storage, a central processor (CPU), etc. FIG. 1 illustrates two types of displays 14, 16; other displays may be used. Display 14 displays each parameter, effacement, cervical dilation, cervix position, station and/or BPD distance, in the form of units of distance (e.g. cm). Display 16, however, is a Partogram, in which the cervical dilatation and the station are displayed in graphical form as a function of time to show the interrelation of the cervical dilatation and the descent of the fetal head (or other presenting part) and in which the effacement and cervical position may also be similarly displayed.

Figure 4:
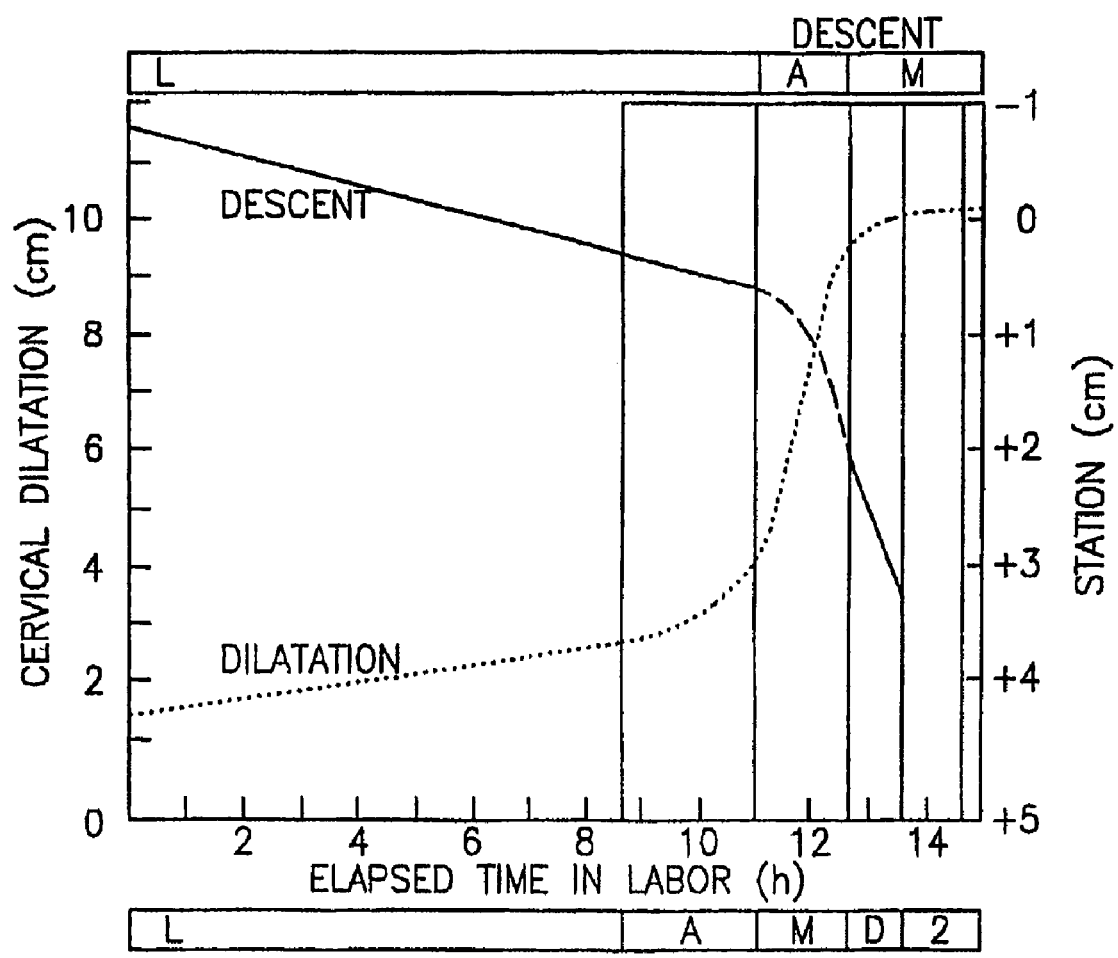
FIG. 4 more particularly illustrates the partogram display in the system of FIG. 1, according to an embodiment of the invention.
Figure 4A:
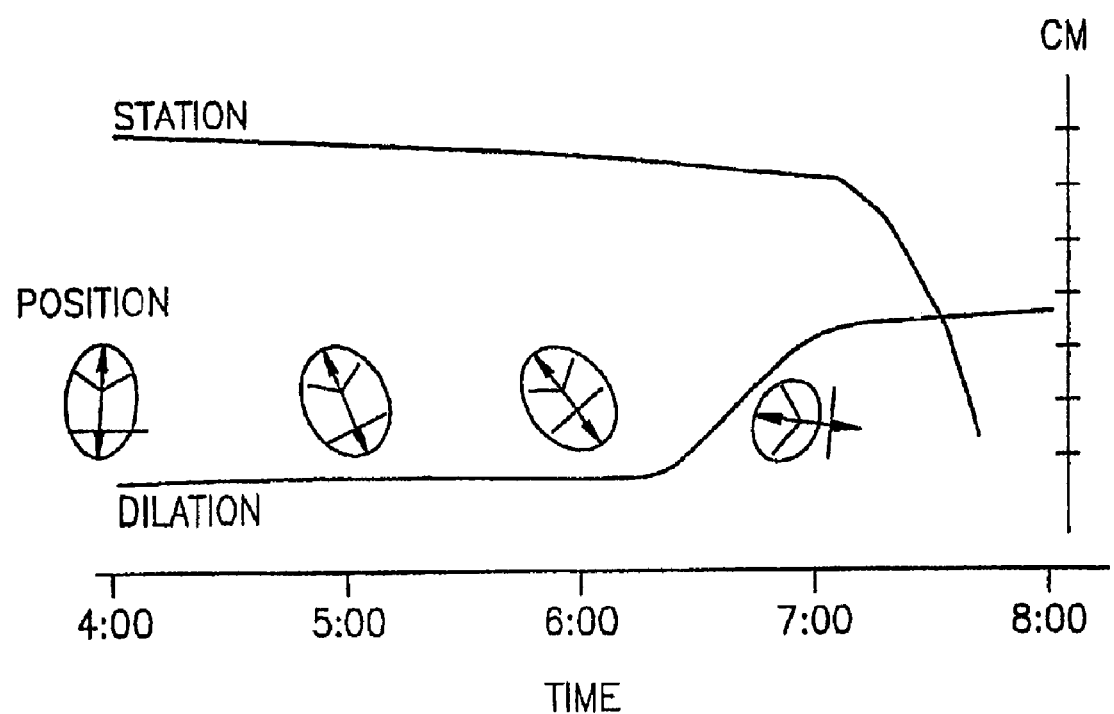
FIG. 4A presents an illustration of a display of position of the presenting part in various stages of labor, in accordance with an embodiment of the present invention.

The Partogram display 16, which is more particularly illustrated in FIG. 4, is of value since it provides a visual display of the progress of labor and can be recorded if desired. By using the Partogram, a better determination can be made whether labor is progressing normally. "Alert" and "action" lines may be printed on the Partogram to provide a visible indication of whether labor is progressing normally or abnormally, and thereby to better alert the attending personnel to take prompt action if necessary. Such an "electronic Partogram" can also markedly reduce the number of prolonged labors, the rate of intrapartum, post partum and early neonatal infections, the number of unnecessary interventions, and neonatal trauma due to wrong assessment of the fetal head. A partogram need not be used, and other types of partograms may be used.

Figure 5:
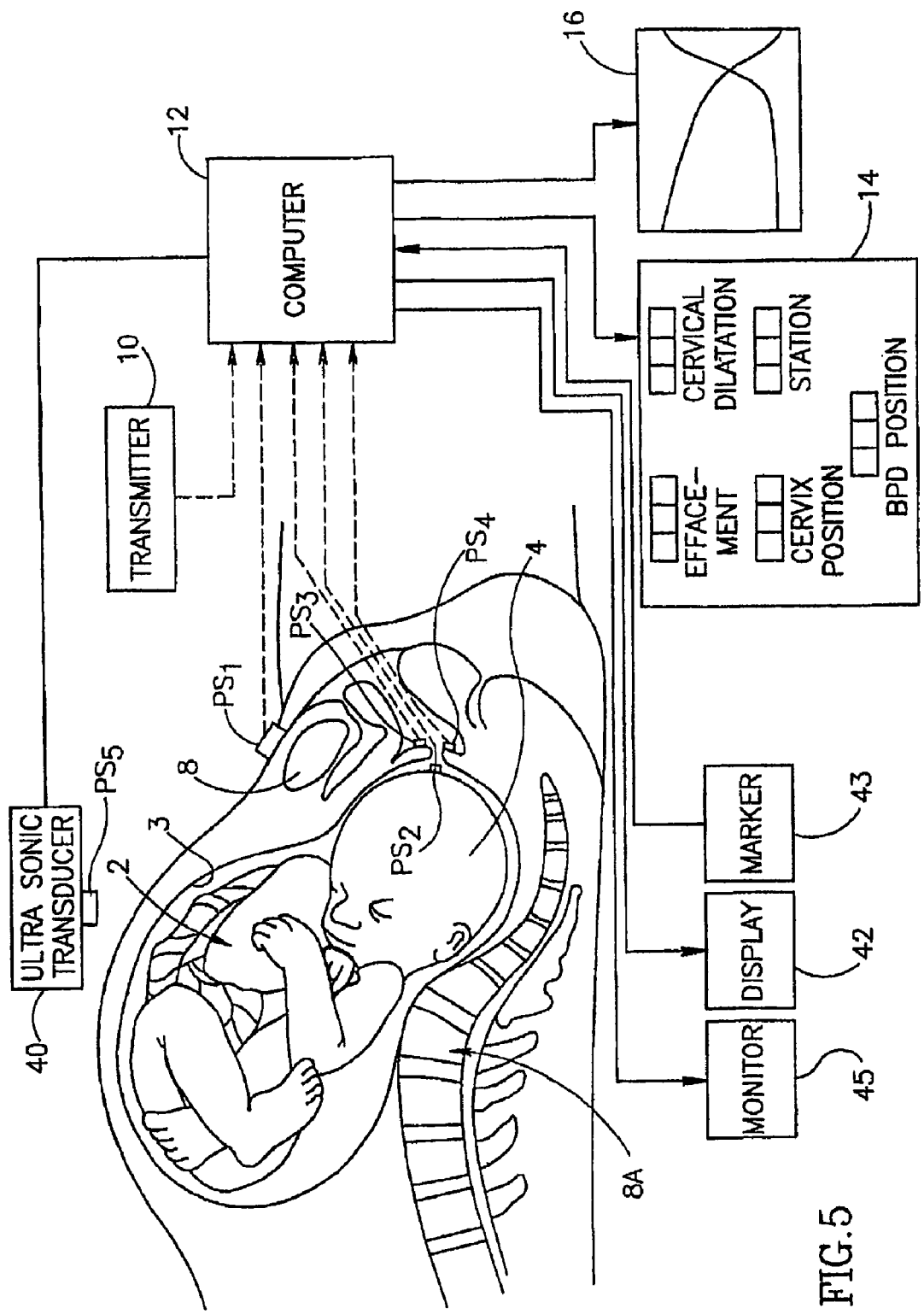
FIG. 5 is a block diagram illustrating an imaging system for displaying the image of the mother's womb, particularly the cervix, pelvic bones, and the fetal head to better show the progress of the labor, according to an embodiment of the invention.
Figure 6A:
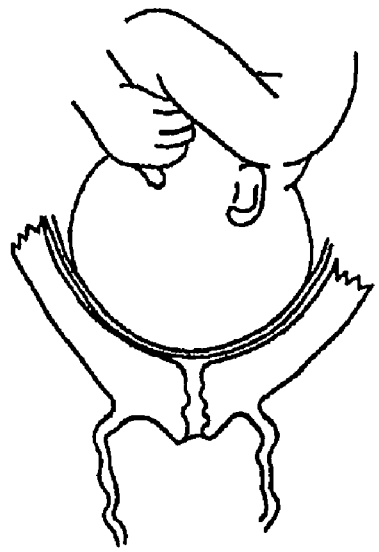
FIGS. 6A-6D illustrate displays produced by the system of FIG. 5 during the various stages of labor, according to an embodiment of the invention.
Figure 6B:
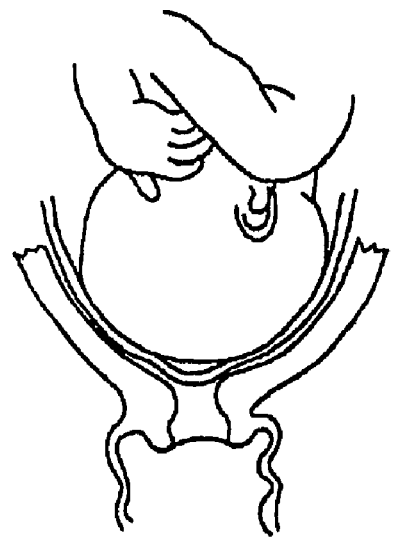
Figure 6C:
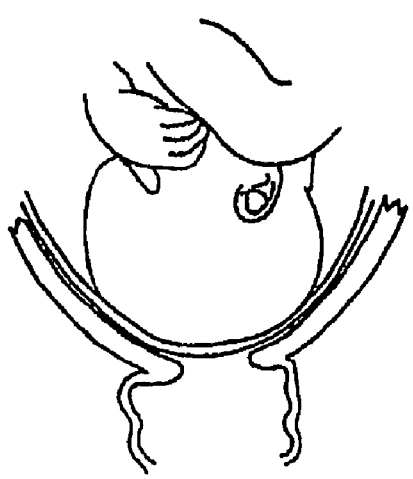
Figure 6D:
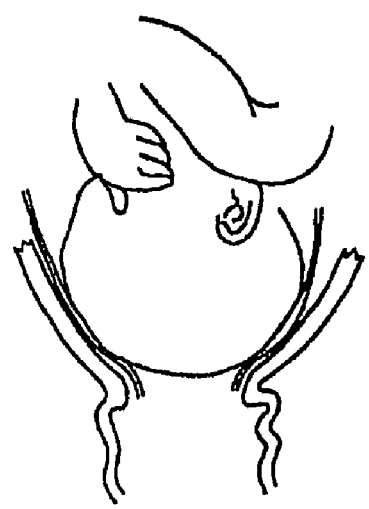

FIG. 5 illustrates a monitoring system similar to that of FIG. 1, further equipped with an imaging system for imaging the womb area of the mother and for continuously displaying, for example, the mother's cervix, pelvic bones, and fetal head (or other presenting part). Other parts may be displayed.

The system of FIG. 5 includes an ultrasonic transducer 40 for imaging the womb area, via the computer 12, on an image display 42. It also includes a position sensor PS5 attached to the ultrasonic transducer 40. Position sensor 1000 may also be used to capture position information for this embodiment. Thus, any point in the image on display 42 may be selected by a marker device 43, such as a mouse or touch screen, and its location fed into the computer 12 to identify the location of the respective point with respect to the location of position sensor PS1 attached to the mother's pubic bones. Other devices, such as a keyboard, may effect the function of the marker device 43. Other or additional locations may be mapped. With this information, the computer 12 can compute the various relationships displayed in displays 14 and 16 (for example), possibly obviating the need for the positions sensors PS2, PS3 and PS4. The image displayed in display 42 may be used in the same manner for marking, for example, the BPD on the fetal head as illustrated in FIG. 8, thereby enabling particularly the spatial distance between the fetal BPD and the pelvic inlet to be computed and monitored. Other computations may be made. It will be appreciated that other reference points, other than the BPD or the tip of the fetus head, as well as any other point of the mother's pelvis, may be used as the reference points for monitoring the progress of the labor. This freedom may be desirable because of the variety of preferences among various physicians.

The imaging system illustrated in FIG. 5 could also be used to, for example, provide a visual image of the various stages of labor, e.g., as illustrated in FIGS. 6A-6D showing the progressive dilatation and effacement of the cervix, or as illustrated in FIGS. 7 and 8 showing the progressive descent of the fetal head tip through the various stations with respect to the ischial spines 7 (FIG. 7) or mother's pelvic inlet (FIG. 8). If the imaging system is used together with all five position sensors PS1-PS5 illustrated in FIG. 5, the ultrasound imaging may be used only to measure the BPD at the beginning of labor or later. Other sets of position sensors, with other positions, and with other configurations, may be used. The computer 12 then determines the distance between the BPD and, for example, the tip of the fetal head, and thereafter it can use the position of the tip of the fetal head also to determine the BPD position. The ultrasound imaging may thereafter be used only for verification if desired. It can also be used to verify cervical dilatation and effacement.

Figure 9:
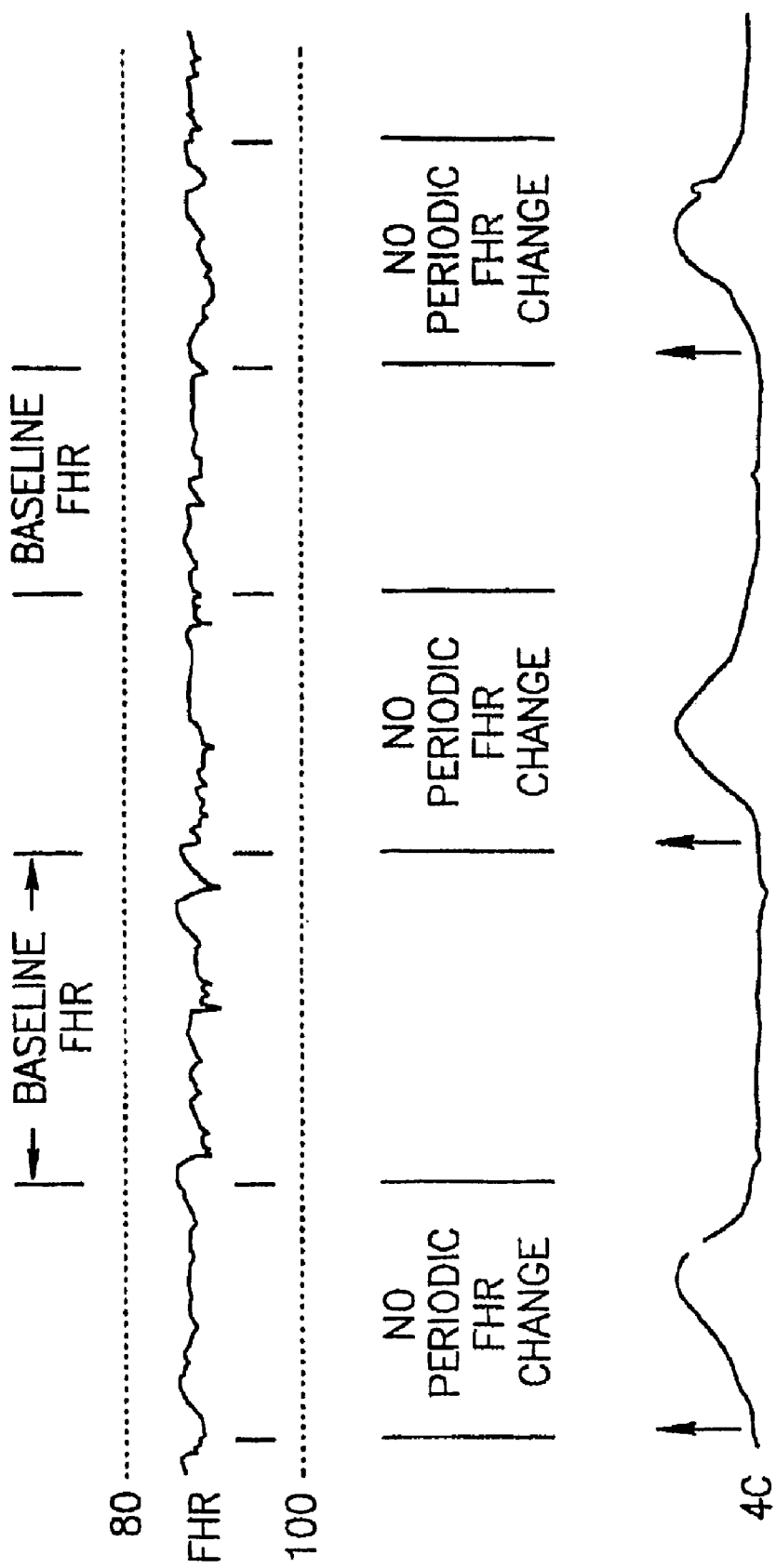
FIG. 9 illustrates a fetal heart monitoring display and uterine contractions that may be included in an embodiment of the invention.

The system illustrated in FIG. 5 may also be used for, for example, sensing contractions in the mother's uterus. During contractions, the fetal head moves slightly, and the dilatation also grows slightly; and after contractions, they both retract to their previous positions. By thus observing the dilatation and/or fetal head position as a function of time, the attending physician may discern the occurrence of contractions as well as the duration and strength of such contractions. The occurrence of contractions may also be detected, for example, by using one or more location sensors attached to the maternal abdominal surface to track the stretching effect on the abdominal surface caused by the contractions. This may be accomplished by analyzing the relative movements between the sensors and a reference sensor, and/or by analyzing the relative motion between the sensors themselves. In addition, by including a heart pulse sensor in the fetal head position sensor PS2, the physician may observe the relation of the fetal heart rate (FHR) in relation to the uterine contractions (UC), to show the relationship between the two as illustrated in FIG. 9. Computer 12 may be programmed to receive the above information from the various sensors and produce, in a monitor 45, a display, for example, corresponding to the fetal heart rate (FHR) in relation to the uterine contractions (UC), as illustrated in FIG. 9. Such information is particularly desirable if the presence of complications is established or anticipated. Other analysis may be possible.

While separate displays are shown in the drawings, it will be appreciated that these displays could be in the form of windows on the same large computer display.

Figure 12:
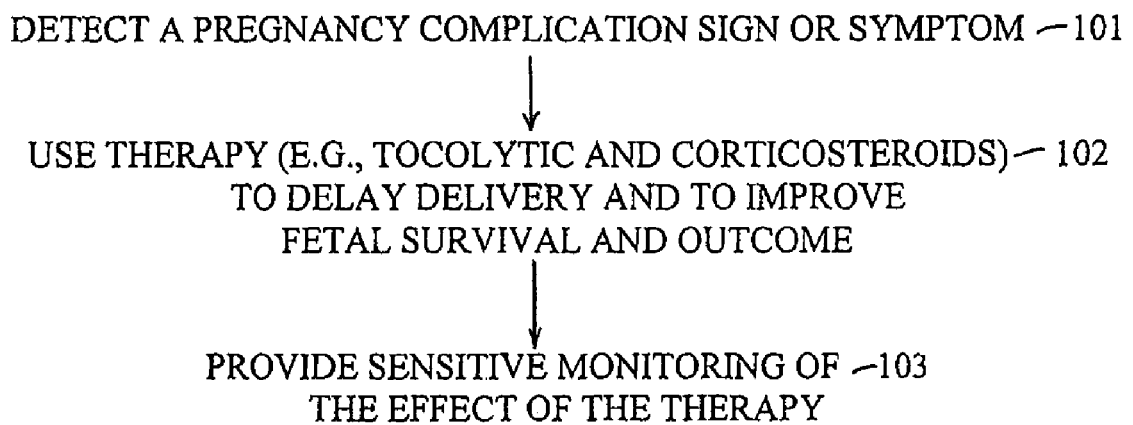
FIG. 12 is a simplified flow chart of using the system of FIG. 1 for early detection of a pregnancy complication, in accordance with an embodiment of the present invention.

Reference is now made to FIG. 12, which illustrates using the system of FIG. 1 for early detection of a pregnancy complication, such as but not limited to, preterm labor or threatened abortion, in accordance with an embodiment of the present invention. "Preterm labor" is defined as labor that occurs before completion of the 37th week of gestation. The incidence of premature birth has not decreased during the past 40 years. In the United States, preterm delivery affects approximately one in 10 births and is the cause of at least 75 percent of neonatal deaths, excluding those related to congenital malformations (McCormick M C. The contribution of low birth weight to infant mortality and childhood morbidity. N Engl J Med 1985; 312:82-90.).

Identification of the symptoms of preterm labor helps ensure that the patient can be evaluated, diagnosed and treated appropriately.

Because the symptoms of preterm labor may be nonspecific, Creasy and Herron suggested criteria of preterm labor (Creasy R K, Herron M A. Prevention of preterm birth. Semin Perinatol 1981; 5:295-302). It is suggested that a diagnosis of preterm labor should be made in a patient between 20 weeks and 36 weeks, six days of gestation if uterine contractions occur at a frequency of four per 20 minutes or eight per 60 minutes, and are accompanied by one of the following: premature rupture of membrane (PROM), cervical dilation greater than 2 cm, effacement exceeding 50 percent, or a change in cervical dilation or effacement detected by serial examinations.

It is noted that the above cited references are mentioned for reference purposes only and the invention is not limited to any material or theory mentioned in those references.

"Threatened abortion" is a condition of pregnancy, occurring generally before the 20-24th week of gestation, which suggests potential miscarriage may take place. Approximately 20% of pregnant women experience some vaginal bleeding, with or without abdominal cramping, during the first trimester. This is known as a threatened abortion. However, most of these pregnancies go on to term with or without treatment. Spontaneous abortion occurs in less than 30% of the women who experience vaginal bleeding during pregnancy.

In the cases that result in spontaneous abortion, the usual cause is fetal death. Fetal death is typically the result of a chromosomal or developmental abnormality. Other potential causes include infection, maternal anatomic defects, endocrine factors, immunologic factors, and maternal systemic disease.

Increased risk is associated with women over age 35, women with systemic disease (such as diabetes or thyroid dysfunction), and those with a history of three or more prior spontaneous abortions.

Threatened abortion diagnosis generally involves a pelvic examination that reveals a cervix that is neither thinned (effaced) nor open (dilated). The presence of effacement and/or dilation is consistent with impending miscarriage. A pregnancy ultrasound may be used to detect fetal heartbeat.

Activity restrictions vary from avoiding some forms of exercise to complete bed rest. Restricting activity may not guarantee that a miscarriage will not occur. Healthcare providers typically recommend pelvic rest (abstaining from intercourse, douching, tampon use) until symptoms resolve. The woman's condition may be monitored carefully. Progesterone administration may be used to relax the uterus.

Accordingly, the system may detect a pregnancy complication sign or symptom (step 101, FIG. 12). The signs and symptoms (the terms being used interchangeably) that appear to predict the pregnancy complication (e.g., preterm labor) may include, without limitation, frequent contractions (more than four per hour), cramping, pelvic pressure, excessive vaginal discharge, backache and low back pain.

The system of FIG. 1 may identify even small movements of the cervix during contractions (e.g., 1 mm), and may thus easily detect the above pregnancy complication signs or symptoms, and provide early identification of effective contractions before cervical dilatation and effacement occur.

Once the diagnosis of the pregnancy complication is suspected, therapy, such as but not limited to, tocolytic and corticosteroids therapy, may be used to delay delivery and to improve fetal survival and outcome (step 102, FIG. 12). The system may provide sensitive monitoring of the effect of the tocolytic therapy, which may enable using the minimal effective dose and avoid dose related side effects (step 103, FIG. 12).

Figure 13:
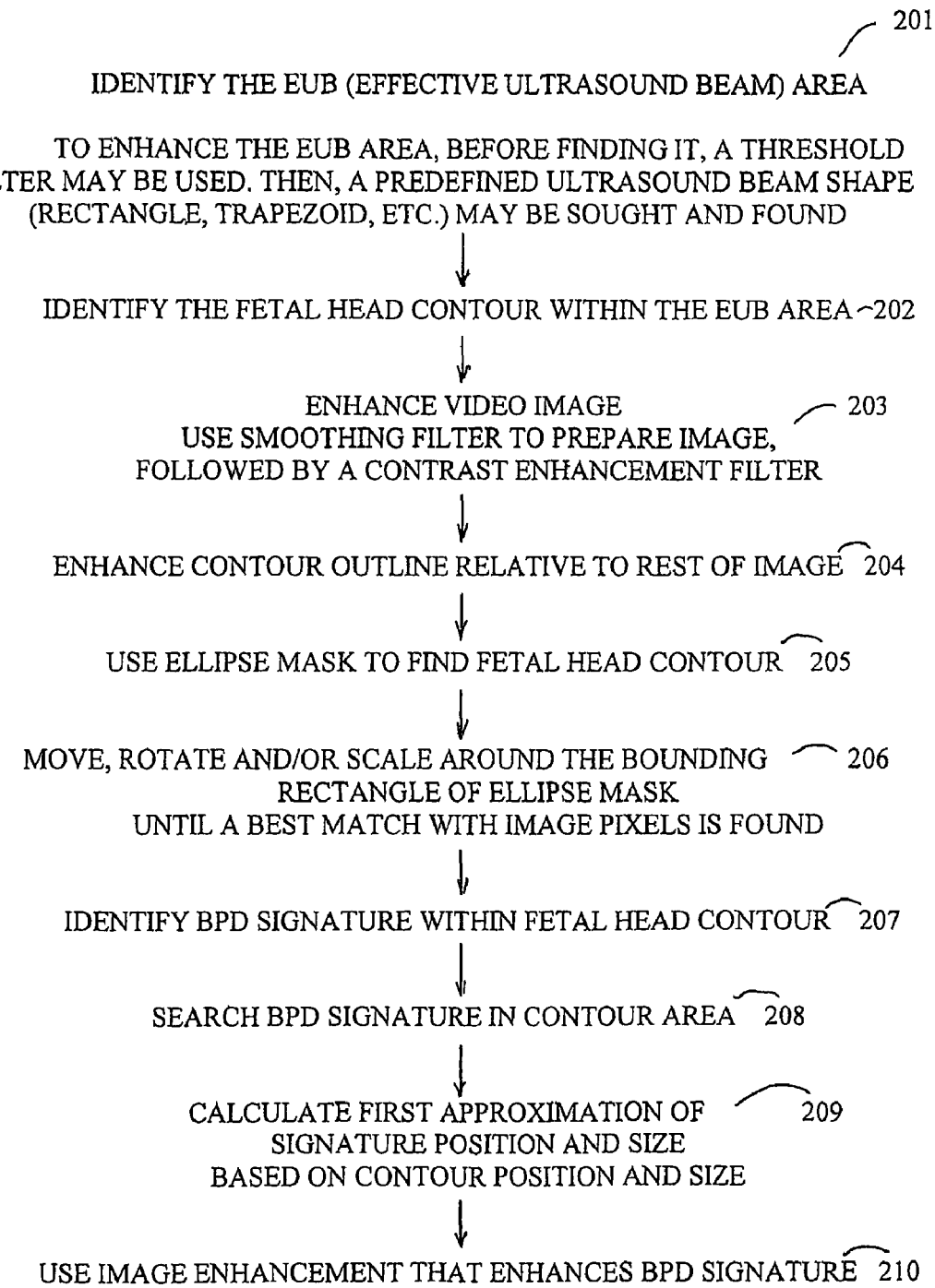
FIG. 13 is a simplified flow chart of a method for identifying a BPD pattern in an ultrasound image, in accordance with an embodiment of the present invention.

Reference is now made to FIG. 13, which illustrates a method for identifying a BPD pattern in an ultrasound image, in accordance with an embodiment of the present invention.

The BPD plane or pattern may be found using image processing of an ultrasound image, such as one obtained by the system of FIG. 1. This may be accomplished by the following steps:

1. Identify the EUB (effective ultrasound beam) area (step 201, FIG. 13). This may be equivalent to the Effective Radiating Area (ERA)—beam area at the applicator face.

This step may provide a first approximation of the fetal head contour position and may accelerate further calculations. It may also help extract (and discard) other ultrasound synthetic elements (e.g., text, menu, etc.).

To enhance the EUB area, before finding it, a threshold filter may be used. Then, a predefined ultrasound beam shape (rectangle, trapezoid, etc.) may be sought and found.

2. Identify the fetal head contour within the EUB area (step 202, FIG. 13).

This step locates the fetal head contour and provides a first approximation for any internal pattern searched for in the fetal head. It helps extract (and discard) ultrasound video elements that reside outside the fetal head.

To enhance the video image, a smoothing filter may prepare the image, followed by a contrast enhancement filter (step 203). The contour outline may accordingly be sufficiently enhanced relatively to the rest of the image (step 204). This may mean that only a partial contour is available, and typically the horizontal edges may be enhanced. A histogram of the enhanced image, which comprises horizontal and vertical boxes, parallelograms or rectangles in the area of the fetal head contour, may provide a first approximation for a bounding rectangle of the fetal head contour.

An ellipse mask (an ellipse with a thick border) may then used to find the fetal head contour (step 205). The starting size and position of the ellipse mask is based on the bounding rectangle found. The ellipse mask may then be moved, rotated and/or scaled around the bounding rectangle until a best match with image pixels is found (step 206). Ellipse mask parameters (position, size, orientation) define the fetal head contour.

A detailed example of using an ellipse mask to find the fetal head contour is described hereinbelow with reference to FIG. 14, which describes an approximation of the fetal head by a three-dimensional ellipsoid using two-dimensional ultrasound images of various fetal head cross-sections.

3. Identify the BPD signature within the fetal head contour (step 207, FIG. 13).

The fetal head contour has been found as described above. Now, a BPD signature is searched in the contour area, wherein the contour diameter is the symmetric axes of the signature (step 208). The position and size of the BPD signature are approximately proportional to the contour size.

To find the BPD signature, a first approximation of the signature position and size is calculated based on the contour position and size (step 209). An image enhancement that enhances the BPD signature is used (step 210). A model of this signature composed of pre-defined geometric shapes (e.g. two parallelograms) may be used to do pattern matching and find the BPD signature. The symmetric nature of the BPD signature across the ellipse diameter is used for enhancement of this model.

Figure 14:
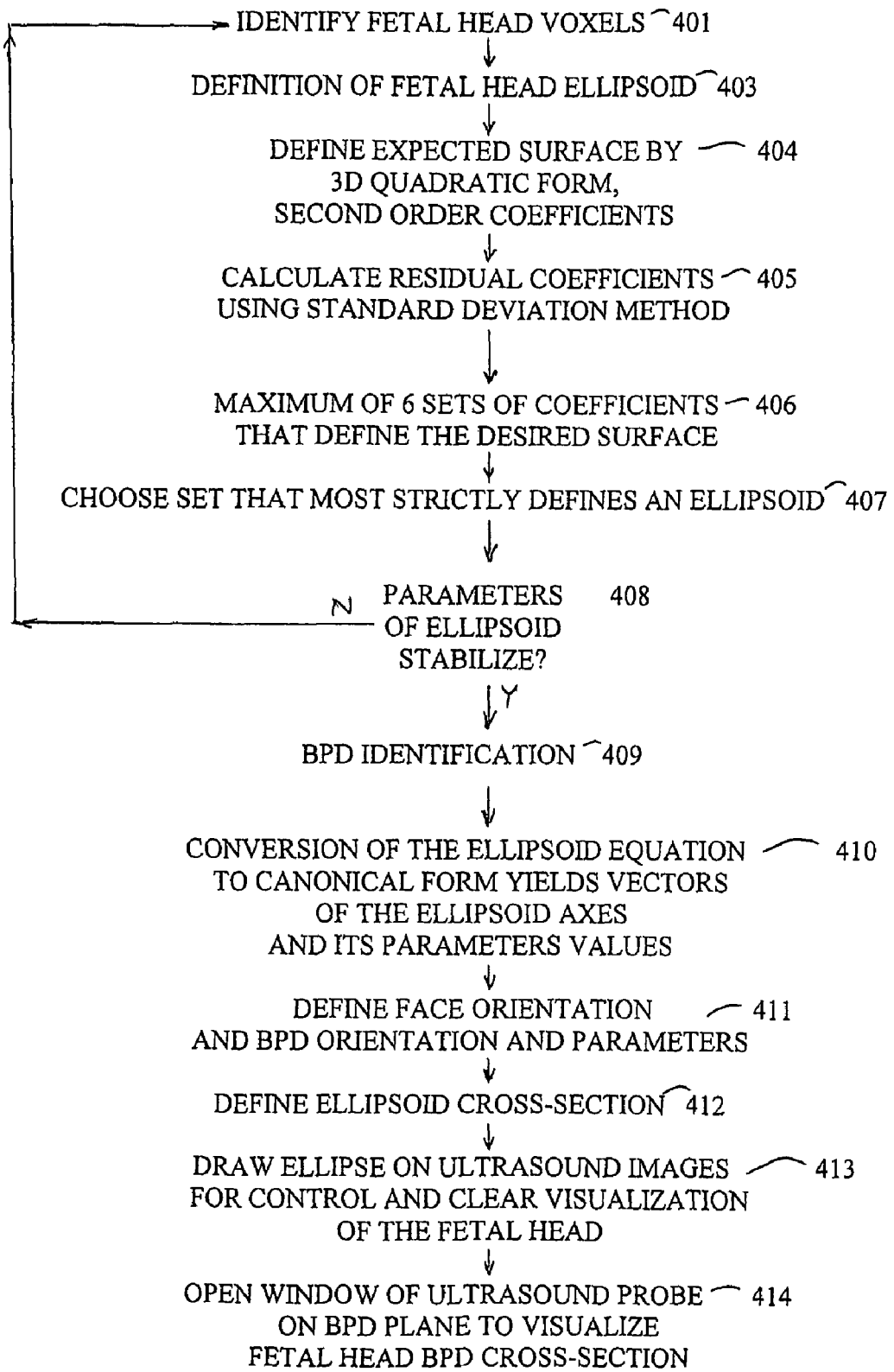
FIG. 14 is a simplified flow chart of a method of approximating the fetal head by a three-dimensional ellipsoid using two-dimensional ultrasound images of various fetal head cross-sections, in accordance with an embodiment of the present invention.

Reference is now made to FIG. 14, which describes an approximation of the fetal head by a three-dimensional ellipsoid using two-dimensional ultrasound images of various fetal head cross-sections, in accordance with an embodiment of the present invention. This may be accomplished by the following steps:

1. Identifying the fetal head voxels (step 401), such as by image processing. For example, a set of known image conversion filters may be applied on the 2D images of the fetus head identifying the voxels (or pixels) that belong to fetal head. These voxels may be recorded with their space coordinates in the transmitter coordinate system.

2. Definition of the fetal head ellipsoid (step 403) using the voxels (or pixels) identified in step 402.

This ellipsoid may be defined by general 3D surface coefficients according to the following considerations:

a. The expected surface may be defined by 3D quadratic form, second order coefficients (step 404). In the equation of quadratic form, there are six coefficients of coordinate multiplication factors that correspond to the second order. At least one of these coefficients is different from zero, and as a default, its value may be set to 1.

b. The residual coefficients may be calculated using a standard deviation method (step 405).

c. This results in a maximum of 6 sets of coefficients that define the desired surface (step 406).

d. From these 6 sets of coefficients, the set that most strictly defines an ellipsoid is chosen (step 407).

3. Management of ellipsoid definition (step 408)

Steps 401-407 may be repeated until the parameters of the ellipsoid stabilize and do not depend on new fetal head pixels extracted from additional ultrasound images.

4. BPD identification (step 409)

Conversion of the ellipsoid equation to canonical form yields vectors of the ellipsoid axes and its parameters values (step 410).

In particular, the parameters of main ellipsoid axis may be obtained. Using data from the fixed reference sensor, located proximal to fetal head tip, the head's orientation (top/bottom) may be obtained.

Using asymmetry of the identified ultrasound voxels/pixels of the fetal head and/or parts of fetal head, such as the eyes or nose, the face orientation and BPD orientation and parameters may be defined (step 411).

5. Visualization

An ellipsoid cross-section, as defined by an ultrasound plane, is an ellipse that can be defined after transforming the ellipsoid coefficients to the ultrasound plane coordinate system and setting the z-coordinate to zero (step 412). The curve of this ellipsoid cross-section is an ellipse. The ellipse may be drawn on ultrasound images for control and clear visualization of the fetal head (step 413, and such as in steps 205 and 206 in FIG. 13).

6. Ultrasound probe to BPD plane guidance

The BPD orientation and parameters as defined in step 411 may help guide the ultrasound probe directly to the image BPD plane. Accordingly, a special window of the ultrasound probe on the BPD plane may be opened (step 414). Using this window, a doctor or other practitioner may easily make the ultrasound probe and BPD planes coincide for visualization of the fetal head BPD cross-section.

Figure 14A:
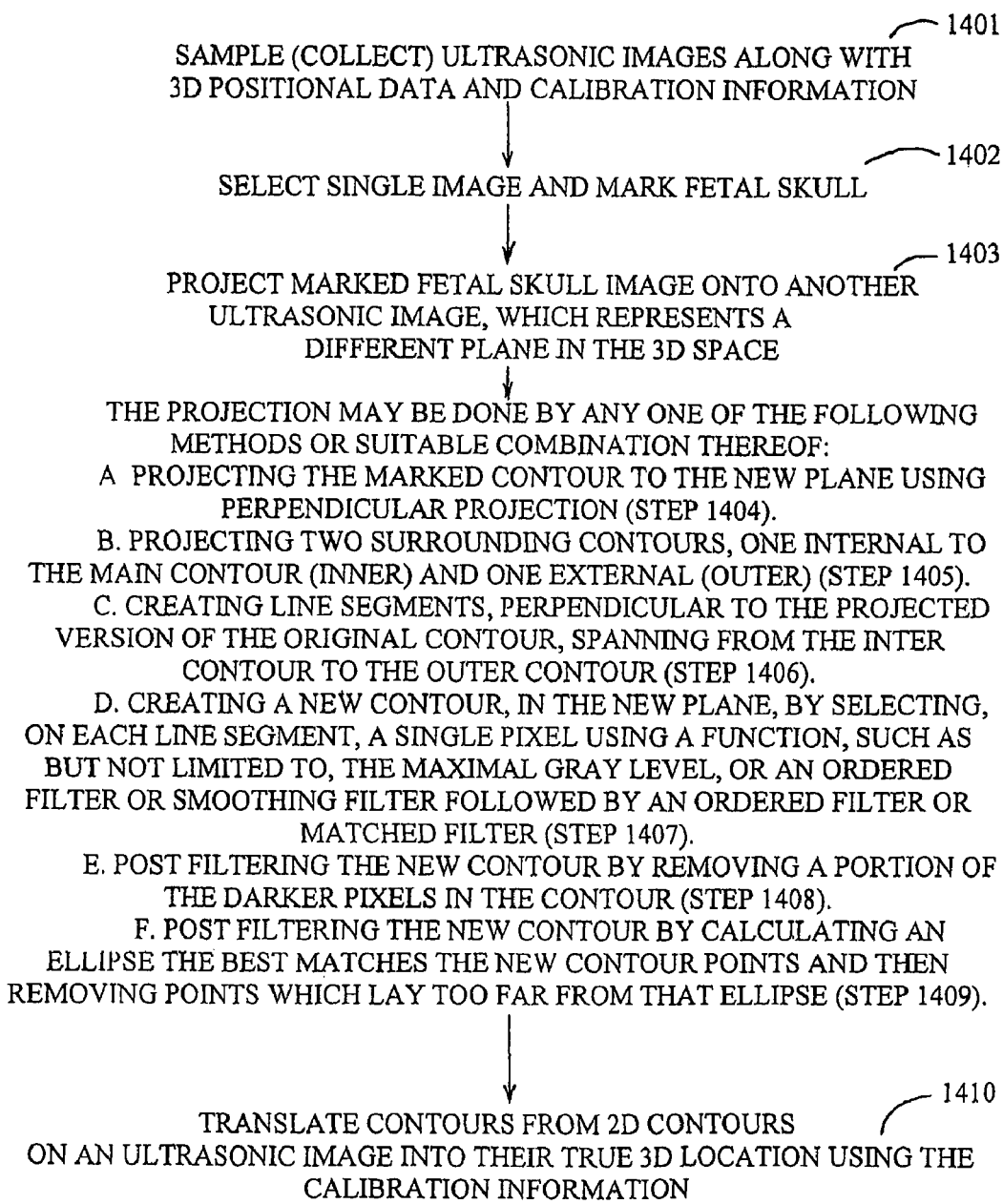
FIG. 14A illustrates a method for BPD reconstruction, in accordance with another embodiment of the present invention.

Reference is now made to FIG. 14A, which illustrates a method for BPD reconstruction, in accordance with another embodiment of the present invention. The method may be used to identify pixels in two-dimensional ultrasonic (US) images that correspond to the fetal skull.

While the physician moves an US transducer looking for images of the fetal skull, ultrasonic images may be sampled (collected) along with 3D positional data and calibration information (step 1401) using known procedures of the art.

After a collection of images is available, a single image may be selected and the fetal skull may be marked (step 1402). This may be accomplished, for example, by the physician manually selecting one of the collected images and marking the contour of fetal skull in the image, or by automatic selection based on image processing algorithms that look for an image with high signal-to-noise ratio and with clear marks of the fetal skull contour. The initial skull mark can also found by means of identifying the fetal head contour within the EUB area (as in step 202, FIG. 13).

The marked fetal skull image may be projected onto another US image, which represents a different plane in the 3D space (step 1403). The projection may be done by any one of the following methods or suitable combination thereof:

a. Projecting the marked contour to the new plane using perpendicular projection (step 1404).

b. Projecting two surrounding contours, one internal to the main contour (inner) and one external (outer) (step 1405).

c. Creating line segments, perpendicular to the projected version of the original contour, spanning from the inter contour to the outer contour (step 1406).

d. Creating a new contour, in the new plane, by selecting, on each line segment, a single pixel using a function, such as but not limited to, the maximal gray level, or an ordered filter or smoothing filter followed by an ordered filter or matched filter (step 1407).

e. Post filtering the new contour by removing a portion of the darker pixels in the contour (step 1408).

f. Post filtering the new contour by calculating an ellipse the best matches the new contour points and then removing points which lay too far from that ellipse (step 1409). The ellipse estimation can be done using least-square methods. Based on the ellipse, new points may be added to the contour for locations where the skull is not evident enough. (Of course this is just one non-limiting example of such post filtering.)

As refinements of the above, selecting the next US image/plane for projection can be done manually, or by selecting the nearest plane (such as with pre-processing that ensures that the selected image contains evidence of the skull, so that the projection is not done on images that do not contain part of the skull or images with a high level of noise).

The contours may then be translated from 2D contours on an US image into their true 3D location using the calibration information (step 1410). This may form a "cloud of points" that may be used to reconstruct a 3D ellipsoid (or similar 3D surface) to estimate the BPD, as described hereinabove with reference to FIGS. 13 and 14.

The method of FIG. 14A is superior to known techniques of the art in that it requires far less computational resources (e.g., compared to well known techniques like "snakes".)

Figure 15:
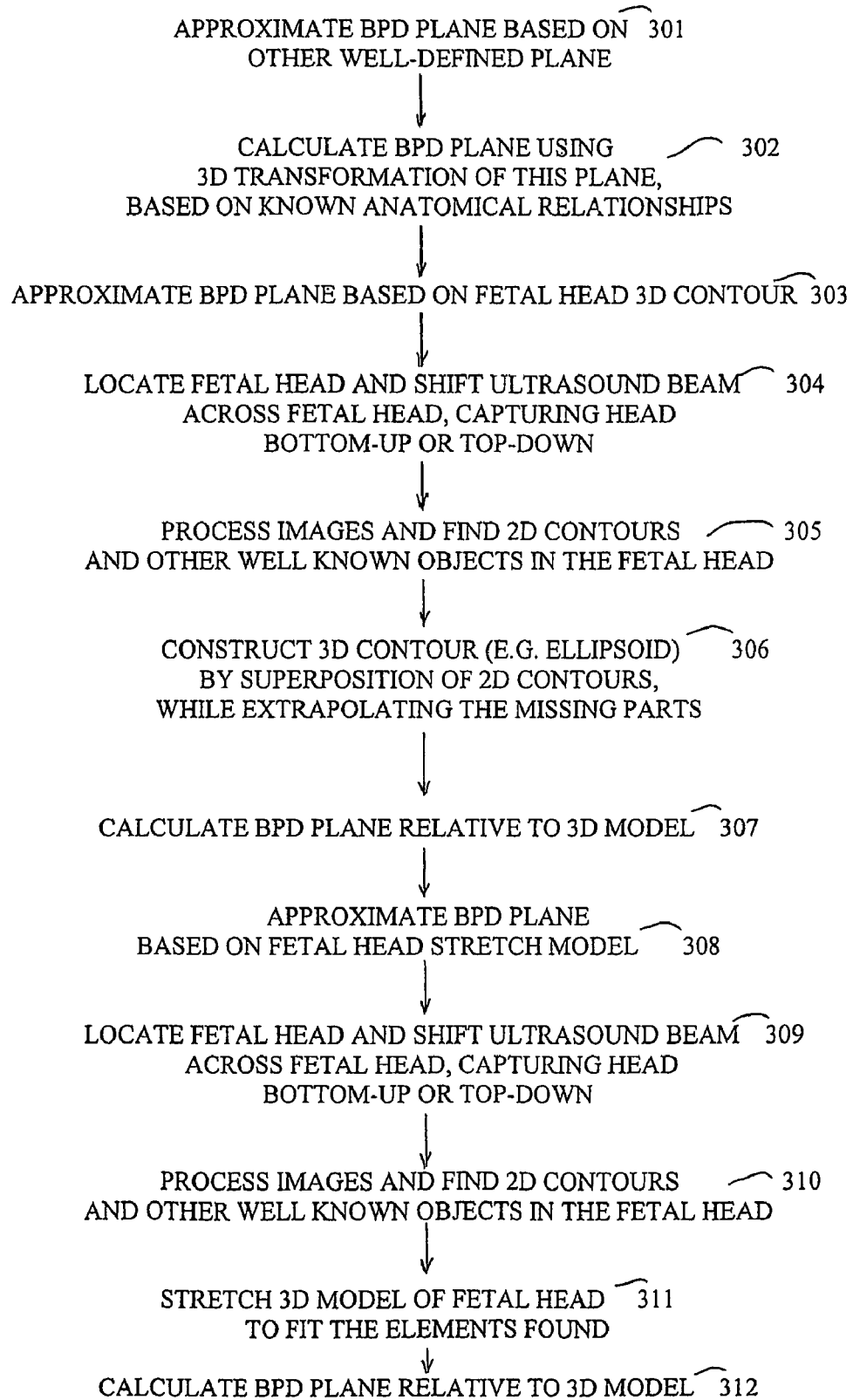
FIG. 15 is a simplified flow chart of a method for BPD plane approximation, in accordance with an embodiment of the present invention.

Methods for BPD plane approximation may be based on other elements in the fetal head, as are now described with reference to FIG. 15.

Method 1: Approximate BPD plane based on other well-defined plane (step 301)

Another well-defined plane in the fetal head, e.g., the sagittal plane, may be located with an ultrasound and tracking device. The BPD plane may be calculated using a simple 3D transformation (shift and rotation) of this plane, based on known anatomical relationships (step 302).

Method 2: Approximate BPD plane based on fetal head 3D contour (step 303)

An ultrasound practitioner may locate the fetal head and then shift the ultrasound beam across the fetal head, capturing head bottom-up or top-down (step 304). This step may collect several 2D images in various places across the fetal head.

An image processing program may then be used to process the images grabbed in the previous step and find 2D contours and other well known objects in the fetal head (step 305).

Since a tracking device is attached to the ultrasound, the contours found in previous steps are well defined in a 3D axes system, and a 3D contour (e.g. ellipsoid) can be constructed by superposition of these 2D contours, while extrapolating the missing parts (e.g. a simple linear extrapolation) (step 306).

After the 3D model is constructed, the BPD plane may be calculated relatively to the 3D model (step 307).

Method 3: Approximate BPD plane based on fetal head stretch model (step 308)

The ultrasound practitioner may locate the fetal head and then shift the ultrasound beam across the fetal head, capturing head bottom-up or top-down (step 309). This step may collect several 2D images in various places across the fetal head.

An image processing program may then be used to process the images grabbed in the previous step and find 2D contours and other well known anatomical objects in the fetal head, such as but not limited to, eyes, vertebral column, mandible, etc. (step 310).

Since a tracking device is attached to the ultrasound, the contours and objects found in the previous step are well defined in a 3D axes system. A 3D model of a fetal head, where such features are marked in the model as well, may be stretched so its size and orientation are changed until a good match is made between the location of the measured features and the location of these features on the model, in the event that the model is not oriented and sized according to the measured fetal head (step 311).

After the 3D model is constructed, the BPD plane is calculated relatively to the 3D model (step 312). In this case, the BPD plane in the fetal head model is stretched with the model and its parameters are well known post stretch.

Figure 16:
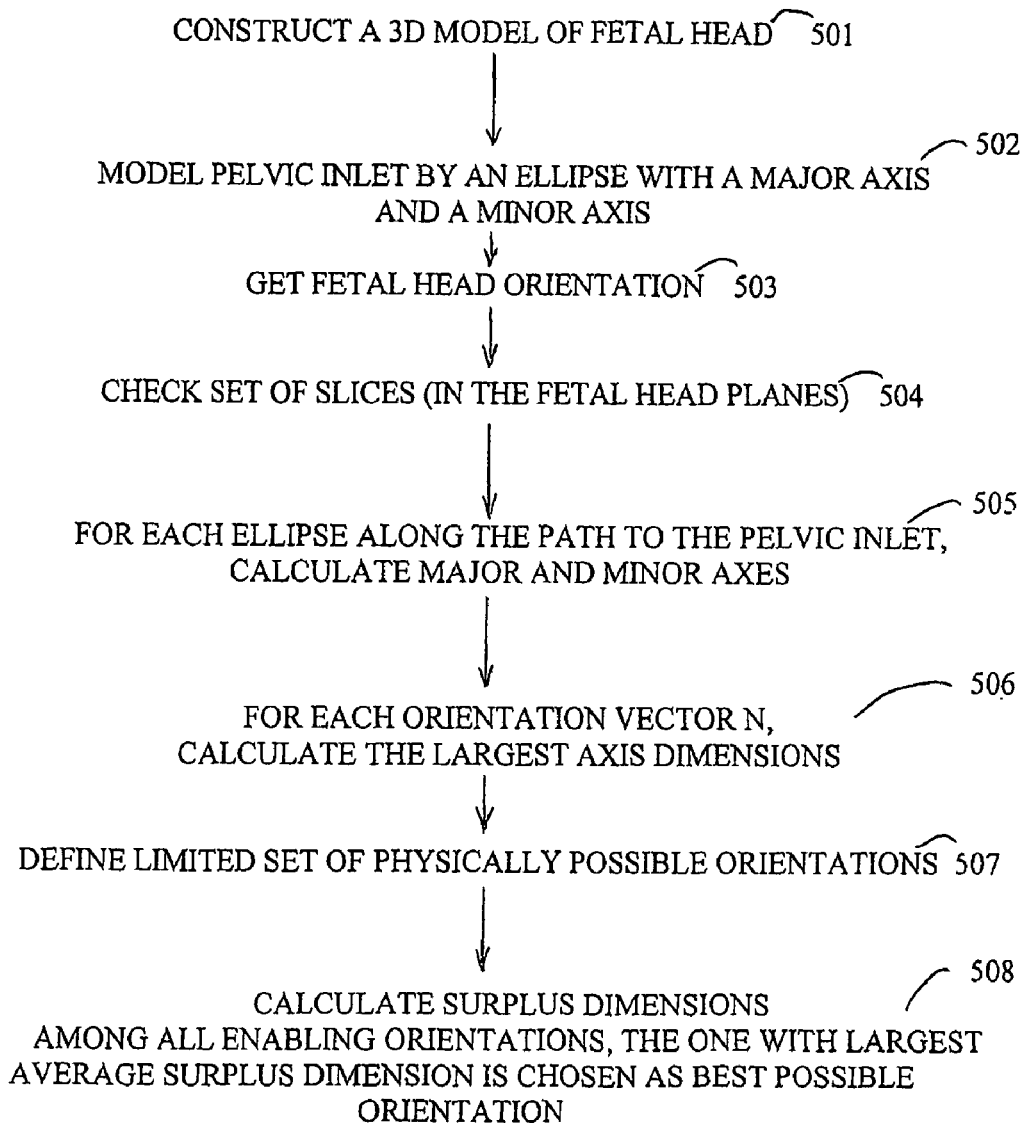
FIG. 16 is a simplified flow chart of a method for identifying the relevant head plane to pass through the pelvic inlet for the specific labor, in accordance with an embodiment of the present invention.

Reference is now made to FIG. 16, which illustrates using the system of FIG. 1 for the identification of the relevant head plane to pass through the pelvic inlet for the specific labor. Normally the best head plane to pass through the pelvic inlet during labor is the BPD plane. However, different factors, such as but not limited to, changes in the shape of the fetal head and complications in labor, may mean that another plane is more favorable for passing through the pelvic inlet. That is, a disproportion may occur between the fetal head and the pelvic inlet (CPD—cephalo-pelvic disproportion). The system of FIG. 1 may be used to perform an early diagnosis of CPD, as is now explained.

First, a three-dimensional model of the fetal head is constructed (step 501) as described hereinabove (e.g., from finding the fetal head contour or from identifying fetal head voxels, etc.). The pelvic inlet may be modeled by an ellipse with a major axis, P, and a minor axis p (step 502). A fetal head orientation is either known or assumed (step 503). In order to verify that the head may pass the pelvic inlet, given the known or assumed orientation, a set of slices (in the fetal head planes) is checked (step 504). A normal N may be defined as the vector pointing perpendicularly from a plane cutting through the fetal head. The normal N is thus an orientation vector for the plane passing through the fetal head. The normal N represents a set of planes, $N_X \cdot X + N_Y \cdot Y + N_Z \cdot Z = c$, wherein the parameter c defines the spatial orientation of the normal N. Slices are collected by changing the parameter c, and their shapes may be modeled by ellipses.

For each ellipse along the path, the major $M_C(N)$, as well as the minor axis $m_C(N)$ may be calculated (step 505). For each orientation vector N, the largest axis $$\text{dimensions } \max_c M_C(N), \max_c m_c(N)$$

may be calculated (step 506).

In searching for the best orientation, a limited set of physically possible orientations may be defined (step 507). Two surplus dimensions may then be calculated:

$S(N) = P - \max M_C(N)$, $s(N) = p - \max m_c(N)$. If both surplus dimensions are positive, the orientation enables passage of head.

Among all enabling orientations, the one with largest average surplus dimension $$\max_N \frac{1}{2}[S(N) + s(N)],$$

is chosen as best possible orientation (step 508).

Figure 17:
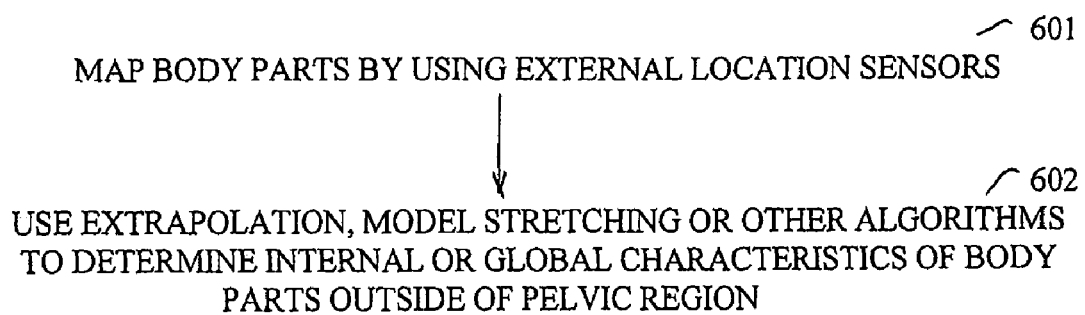
FIG. 17 is a simplified flow chart of a method for the determination of internal or global characteristics of body parts outside of the pelvic region by mapping them using external location sensors and extrapolation, model stretching or other algorithms, in accordance with an embodiment of the present invention.

Reference is now made to FIG. 17, which illustrates using the system of FIG. 1 for the determination of internal or global characteristics of body parts inside and outside of the pelvic region, as well as movements of anatomical structures, in accordance with an embodiment of the present invention. The internal or global characteristics may be determined using integration methods of anatomical planes. Data concerning movement of anatomical structures may be obtained by using temporal analysis of the internal or global characteristics. The body parts may be mapped by using external location sensors (step 601). The mapping may further comprise extrapolation, model stretching or other algorithms (step 602).

Figure 18:
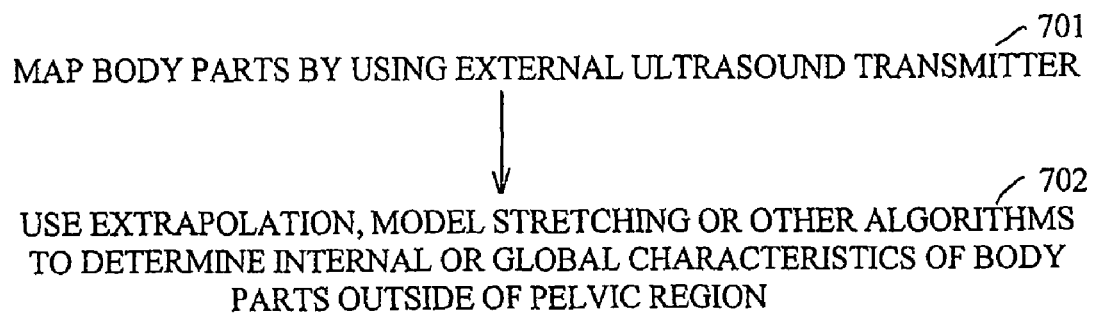
FIG. 18 is a simplified flow chart of a method for the determination of internal or global characteristics of body parts outside of the pelvic region or baby head, by mapping them using external ultrasound transducer and extrapolation, model stretching or other algorithms, in accordance with an embodiment of the present invention.

Reference is now made to FIG. 18, which illustrates using the system of FIG. 1 for the determination of internal or global characteristics of body parts inside and outside of the pelvic region, as well as movements of anatomical structures, in accordance with another embodiment of the present invention. The body parts may be mapped by using an external ultrasound transmitter (step 701). The mapping may further comprise extrapolation, model stretching or other algorithms (step 702).

For both FIGS. 17 and 18, the body parts may include, without limitation, the head, torso (chest), and abdomen. The internal characteristics may include, without limitation, the location of special interest anatomical planes or structures within the body part (e.g. BPD plane in the fetal head). The global characteristics may include, without limitation, volume, weight, size, dimensions, (cross sections) areas, diameters, percentages and the like.

In particular the techniques, which are described in FIGS. 17 and 18, may be used to measure various parameters of the fetus, such as but not limited to, the fetus weight and volume, the fetus head circumference and limb sizes, such as the femur size.

An exemplary implementation of the techniques of FIGS. 17 and 18 is the evaluation of the fetus biophysical profile. The intrapartum assessment of the components of this profile may help predict the fetal wellbeing and influence the perinatal outcome. The effects of biophysical profile tests on pregnancy outcome in high-risk pregnancies have special importance.

The biophysical profile usually includes, but is not limited to, monitoring of fetal movements, fetal tone and fetal breathing, assessment of amniotic fluid volume and assessment of fetal heart rate by electronic monitoring. These parameters, excluding the fetal heart rate, are easily and accurately assessed by the techniques, which are described in FIGS. 17 and 18. The fetal heart rate may be provided by proper connection to a standard delivery monitor.

While the invention has been described with respect to several preferred embodiment, it will be appreciated that these are set forth merely for purposes of example, and that many other variations, modifications and applications of the invention may be made.

What is claimed is:

1. A method for early detection of a pregnancy complication, the method comprising:
    touching a position sensor to a point on a fetal presenting part of a fetus in a mother, and capturing a position of the position sensor;
    touching the position sensor to a set of points on the mother and capturing the position of the position sensor at each point;
    obtaining a correlation of the position of the position sensor on said fetal presenting part to the positions of the position sensor at each point on the mother; and
    detecting a pregnancy complication sign based upon a predefined criterion for said pregnancy complication, wherein said pregnancy complication is related to said correlation.

2. The method according to claim 1, wherein said predefined criterion comprises at least one of contractions with a predetermined frequency, cramping, pelvic pressure, excessive vaginal discharge, back pain, premature rupture of membrane (PROM), cervical dilation greater than a predefined amount, and effacement greater than a predefined amount.

3. The method according to claim 1, wherein said pregnancy complication comprises preterm labor or threatened abortion.

4. The method according to claim 1, further comprising after detecting the pregnancy complication sign, performing therapy to delay delivery and to improve fetal survival and outcome.

5. The method according to claim 4, wherein performing therapy comprises tocolytic therapy.

6. The method according to claim 4, wherein performing therapy comprises corticosteroids therapy.

7. The method according to claim 4, further comprising monitoring an effect of the therapy.

\* \* \* \* \*